United States Patent [19]

Klemarczyk et al.

[11] 4,374,053
[45] Feb. 15, 1983

[54] UNSATURATED ALDEHYDES, ORGANOLEPTIC USES THEREOF AND PROCESS FOR PREPARING SAME

[75] Inventors: Philip T. Klemarczyk, Old Bridge; Robert P. Belko, Woodbridge; Richard M. Boden, Monmouth Beach, all of N.J.

[73] Assignee: International Flavors & Fragrances Inc., New York, N.Y.

[21] Appl. No.: 303,011

[22] Filed: Sep. 17, 1981

[51] Int. Cl.³ ............................................. A61K 7/46
[52] U.S. Cl. ................................. 252/522 R; 568/465; 252/174.11; 424/71
[58] Field of Search ................................... 252/522 R

[56] References Cited

U.S. PATENT DOCUMENTS 4,304,689 12/1981 Boden et al. ............... 252/522 R
4,321,255 3/1982 Boden ...................... 252/522 R Primary Examiner—John F. Niebling
Attorney, Agent, or Firm—Arthur L. Liberman

[57] ABSTRACT

Described is a mixture containing a major proportion of unsaturated aldehydes defined according to the structure:

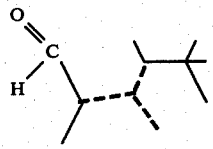

wherein in the mixture in each of the molecules thereof one of the dashed lines represents a carbon-carbon double bond and each of the other of the dashed lines represent carbon-carbon single bonds, prepared by first reacting a diisoamylene compound defined according to the structure:

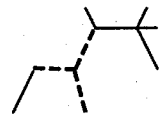

wherein one of the dashed lines represents a carbon-carbon double bond and each of the other of the dashed lines represent carbon-carbon single bonds or defined according to one of the structures:

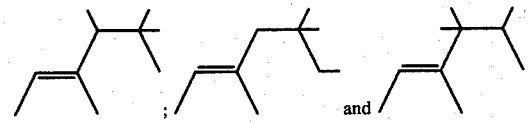

with formaldehyde or a formaldehyde source such as trioxane or paraformaldehyde in the presence of an alkanoic acid anhydride and an acid catalyst; then hydrolyzing the resulting ester or mixture of esters to form an alcohol or mixture of alcohols and finally oxidizing the resulting alcohol or mixture of alcohols to form a mixture of aldehydes; the organoleptic uses of such oxidation products in the field of perfumery, colognes and perfumed articles (e.g., solid or liquid anionic, cationic, nonionic, zwitterionic detergents, fabric softener compositions or dryer-added fabric softener articles).

3 Claims, 19 Drawing Figures

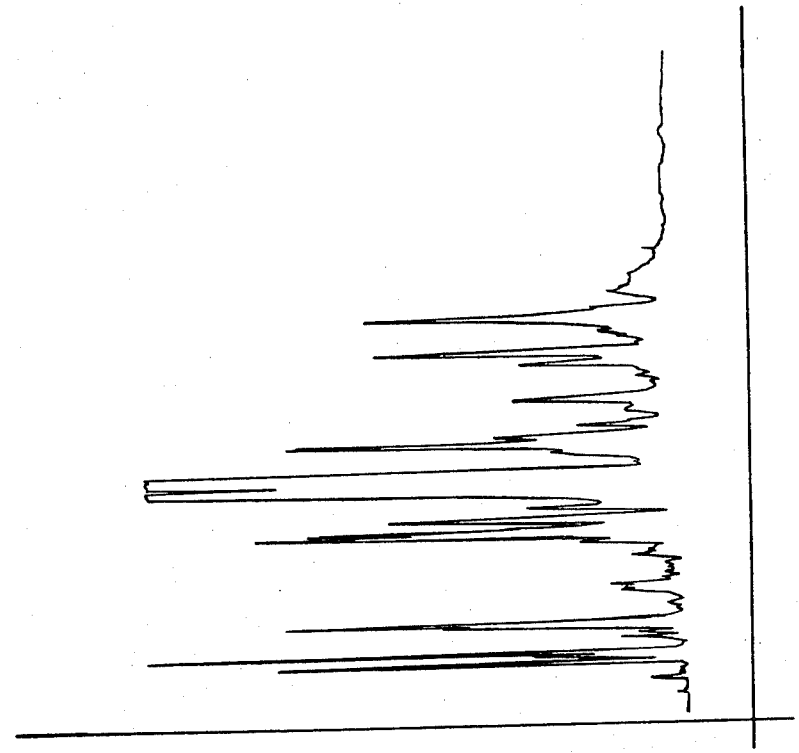
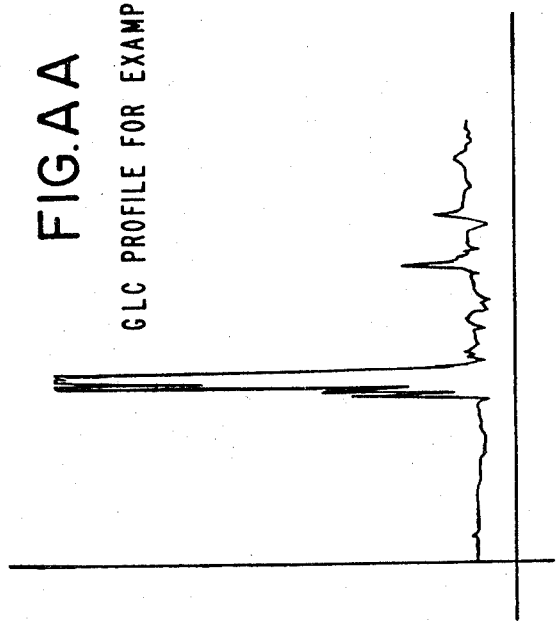
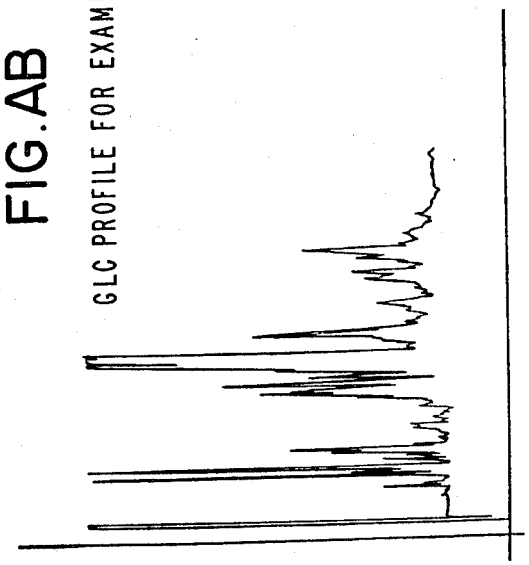

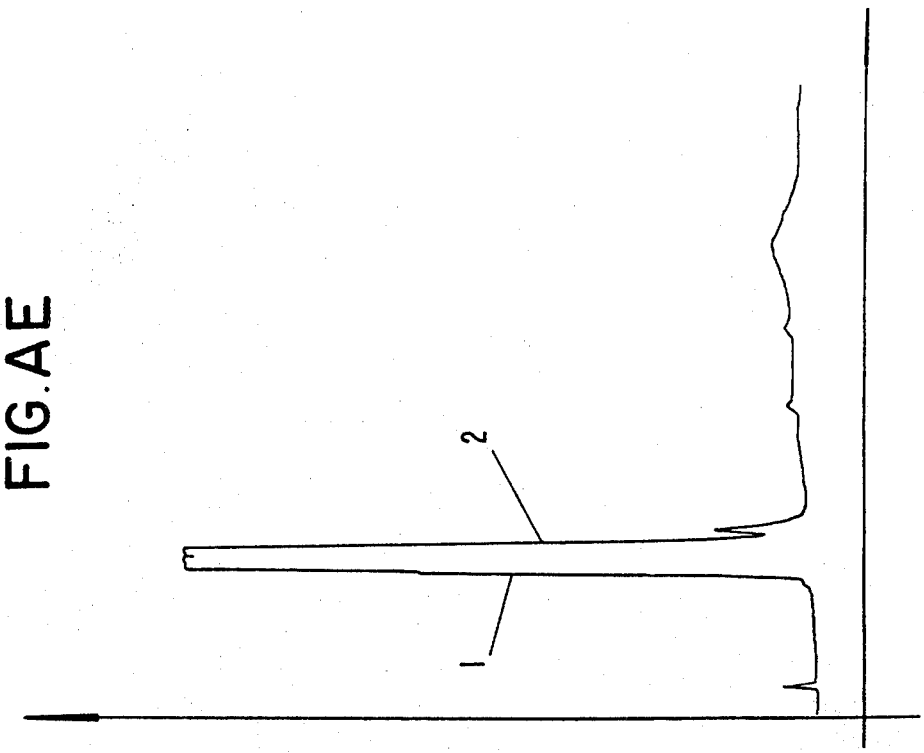
FIG.AE
GLC PROFILE FOR EXAMPLE A. DISTILLATION PRODUCT
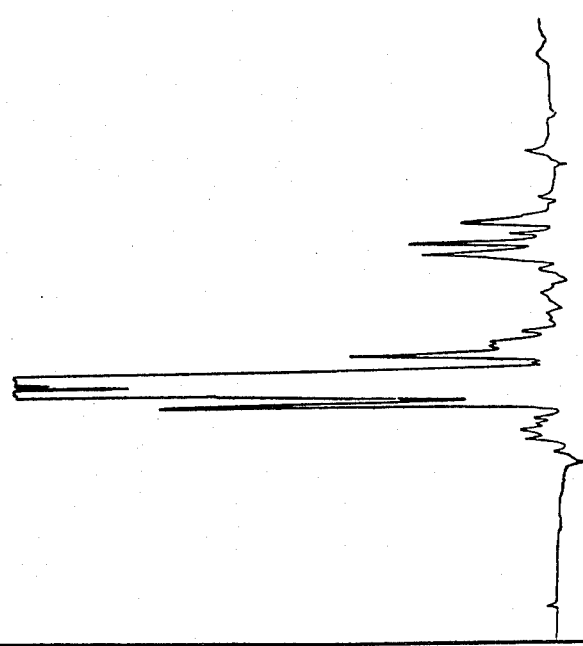
FIG.AD
GLC PROFILE FOR EXAMPLE A CRUDE PRODUCT

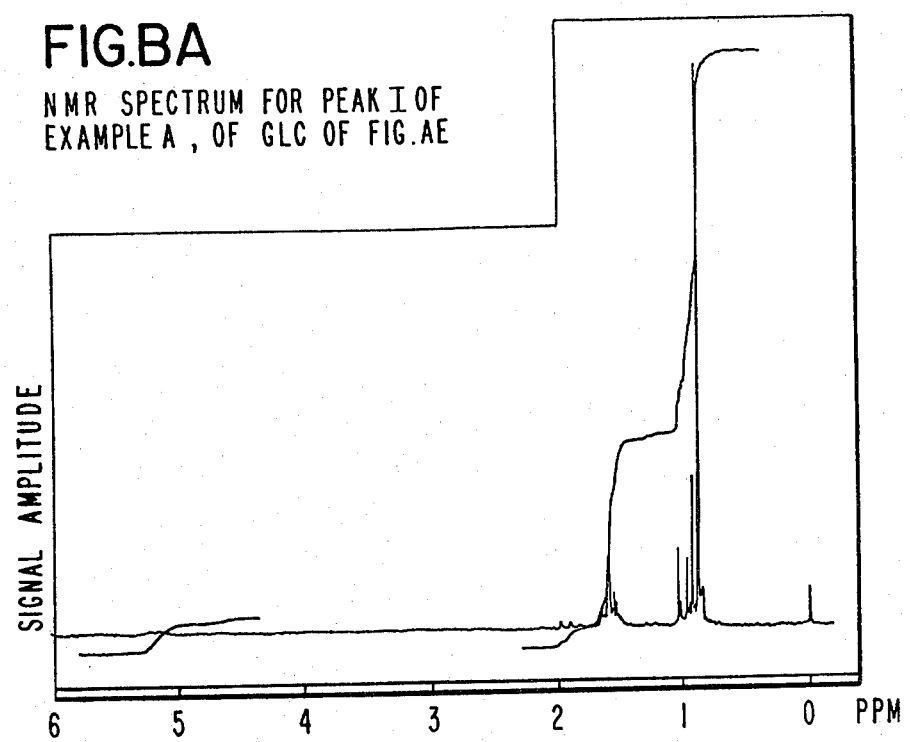
FIG.BA
NMR SPECTRUM FOR PEAK I OF EXAMPLE A, OF GLC OF FIG.AE
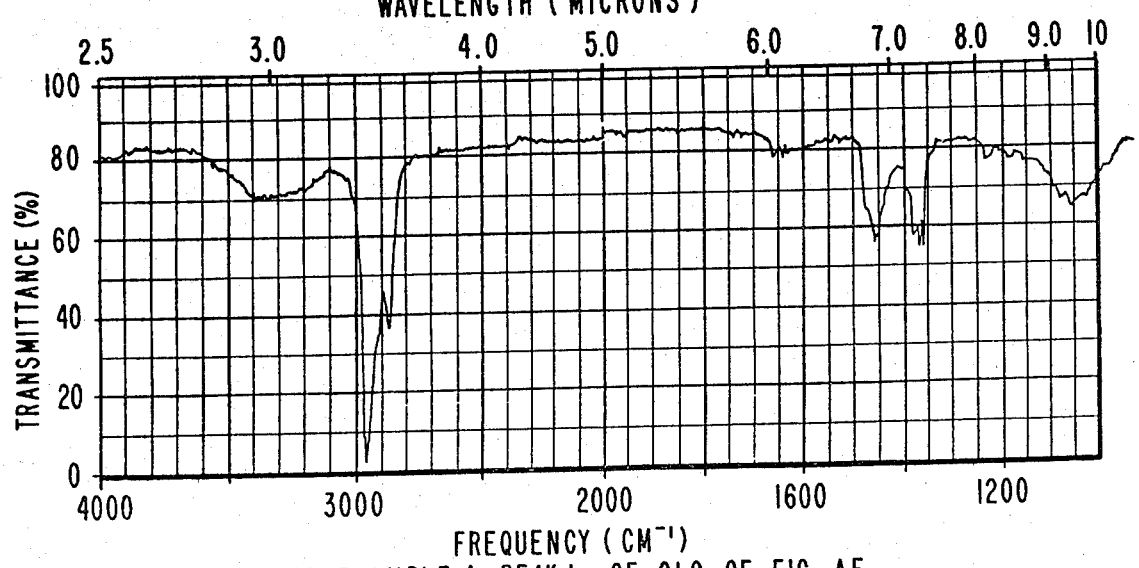
IR SPECTRUM FOR EXAMPLE A, PEAK I, OF GLC OF FIG.AE.
FIG.BB

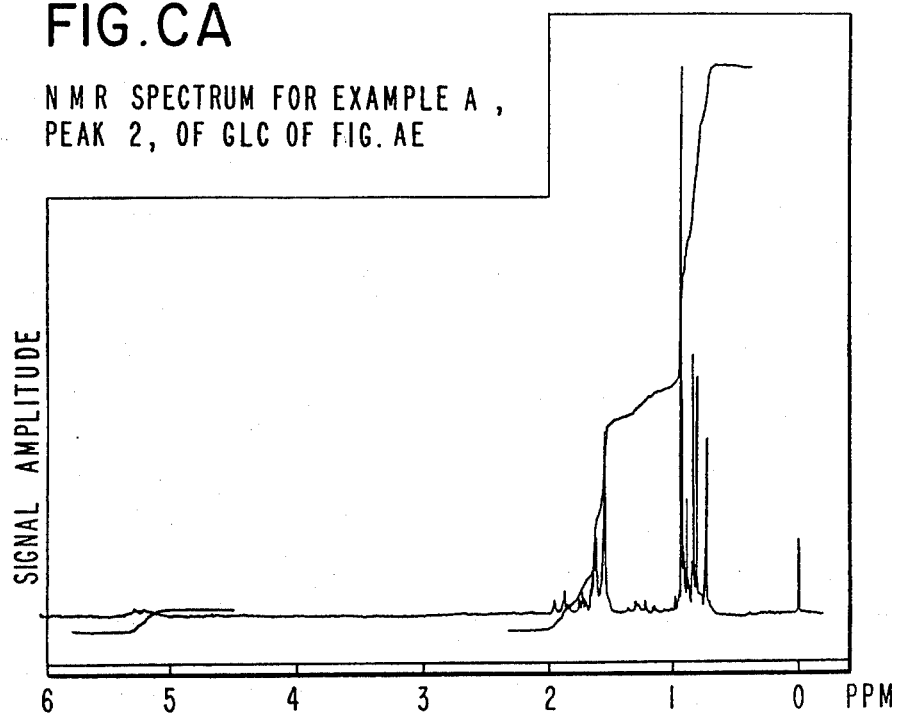
FIG.CA
NMR SPECTRUM FOR EXAMPLE A, PEAK 2, OF GLC OF FIG.AE
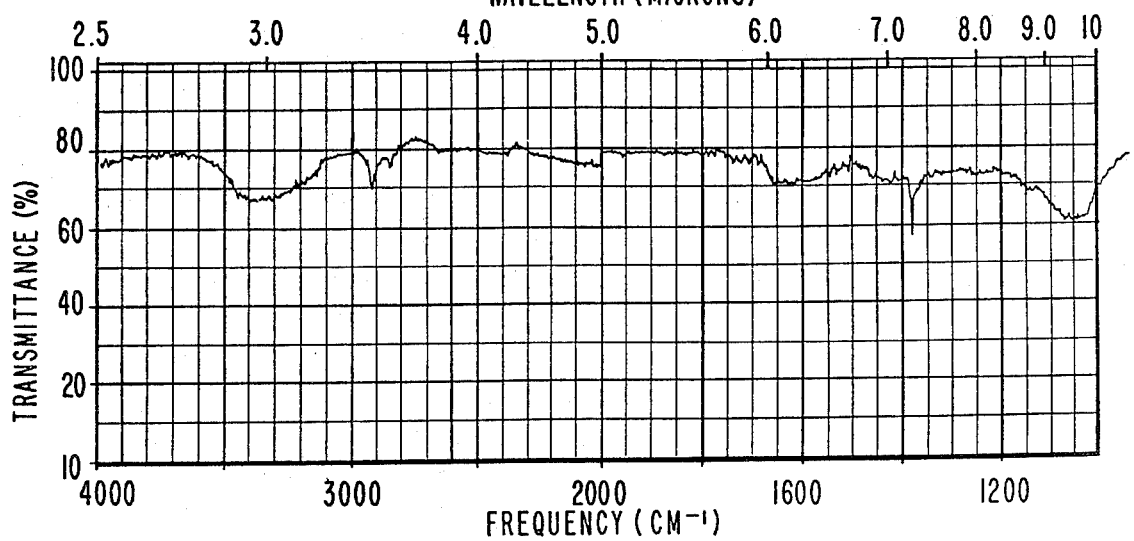
IR SPECTRUM FOR EXAMPLE I, PEAK 2 OF GLC OF FIG.AE
FIG.CB

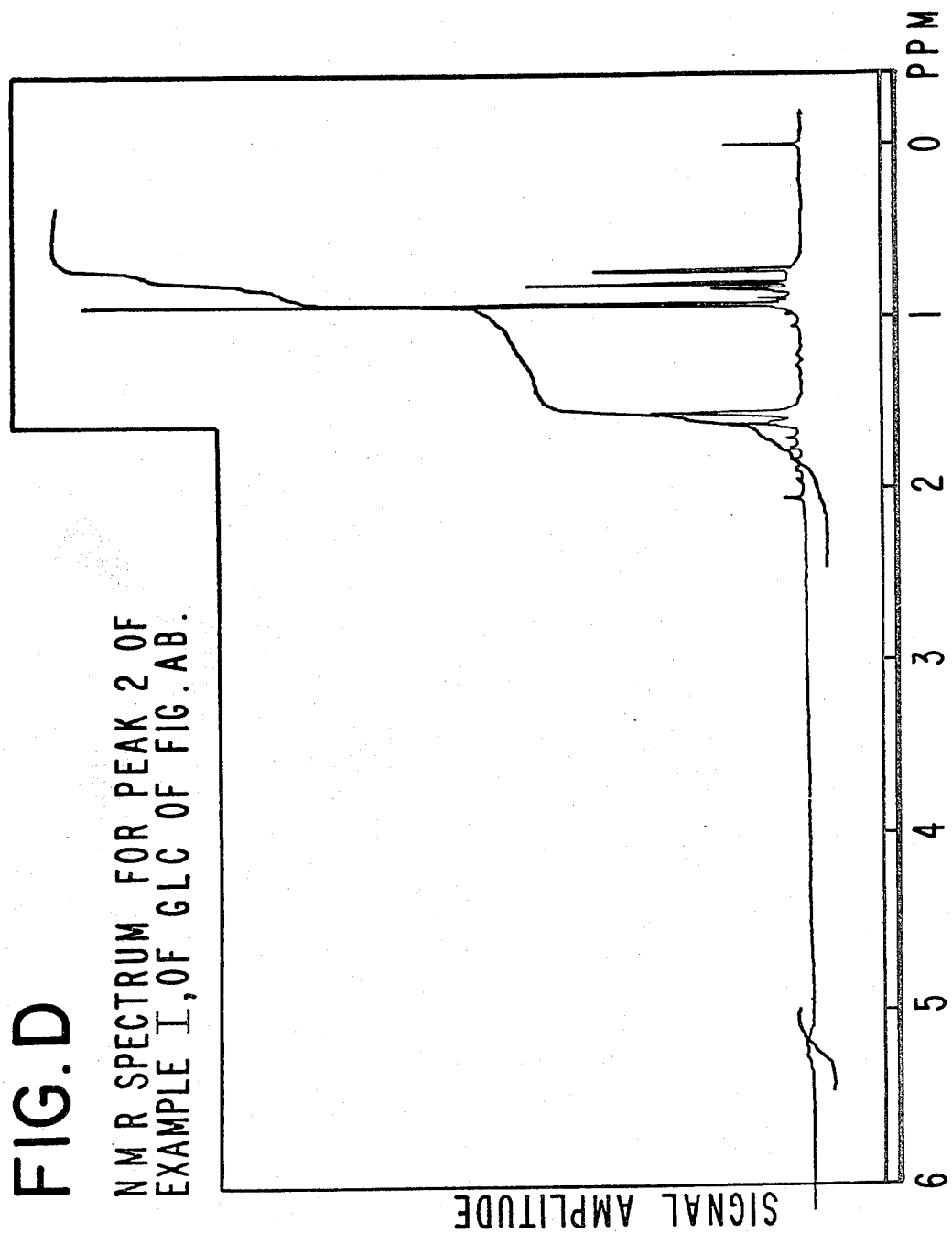
FIG. D
NMR SPECTRUM FOR PEAK 2 OF EXAMPLE I, OF GLC OF FIG. AB.

GLC PROFILE FOR BULKED FRACTIONS 10-17 OF EXAMPLE I.

GLC PROFILE FOR BULKED FRACTIONS 10-17 OF EXAMPLE I.

GLC PROFILE FOR EXAMPLE II.

GLC PROFILE FOR EXAMPLE II.

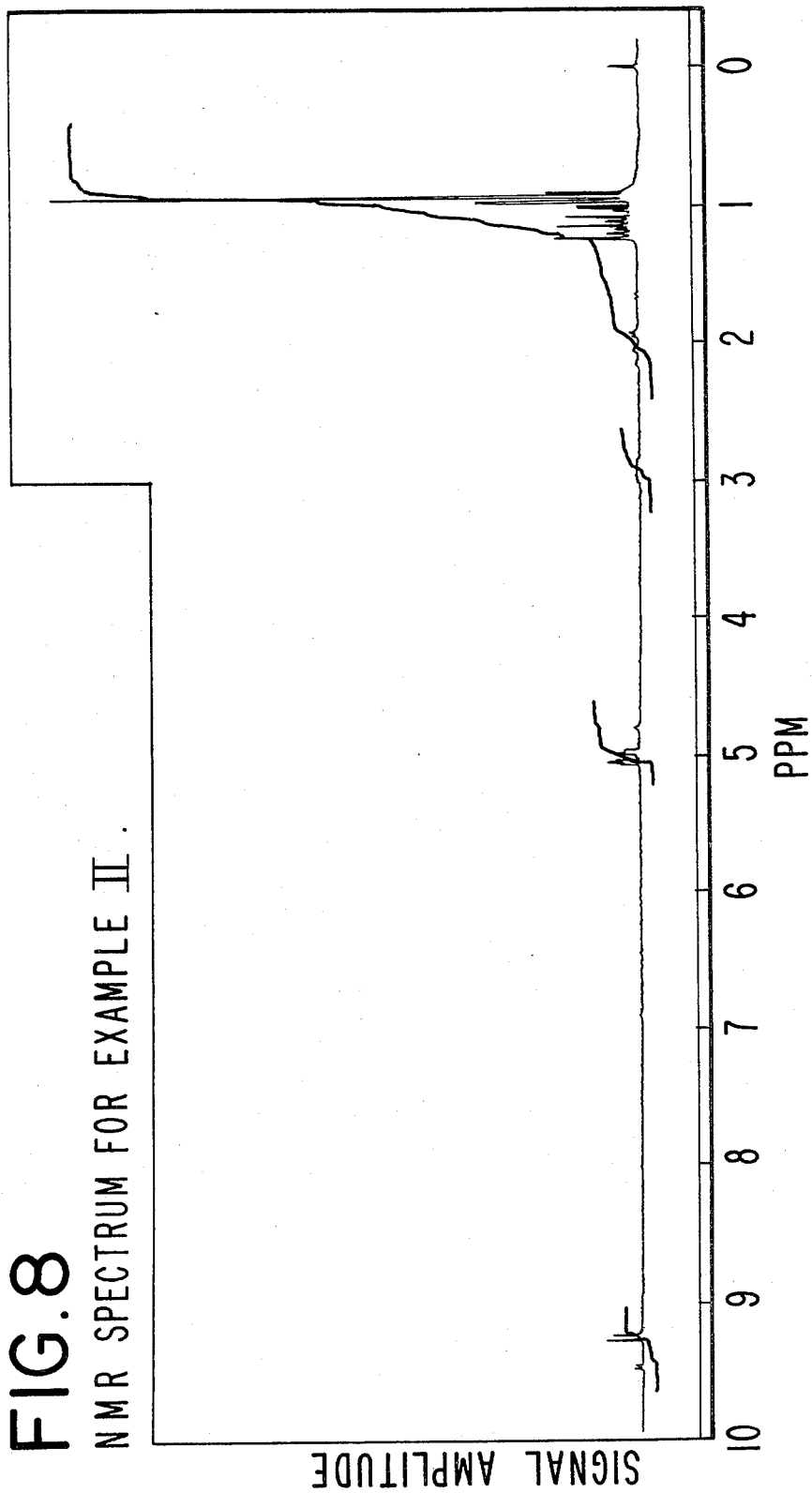
FIG. 8 NMR SPECTRUM FOR EXAMPLE II.

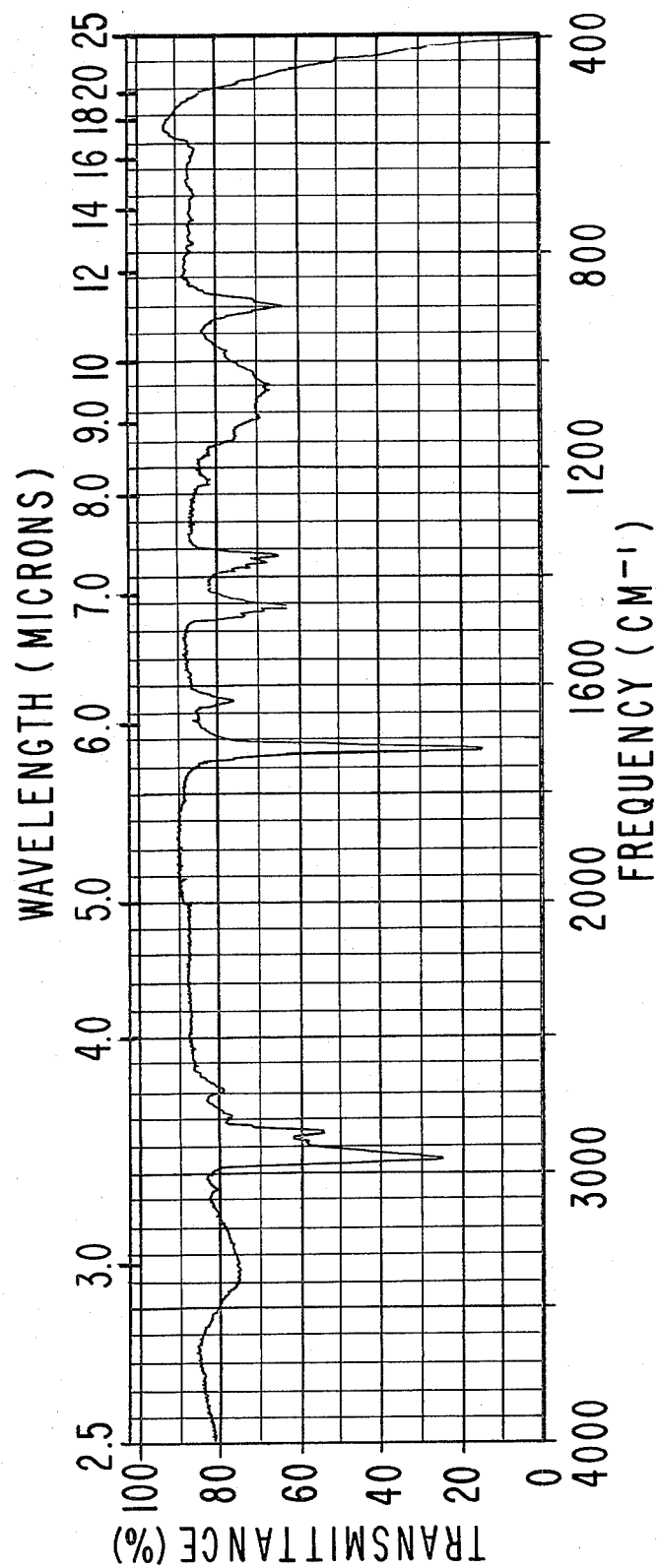

UNSATURATED ALDEHYDES, ORGANOLEPTIC USES THEREOF AND PROCESS FOR PREPARING SAME

BACKGROUND OF THE INVENTION

The instant invention relates to a mixture of compounds containing a major proportion of compounds defined according to the structure:

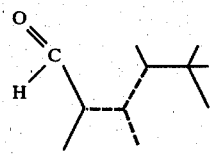

wherein in the mixture in each of the molecules one of the dashed lines represents a carbon-carbon double bond and each of the other of the dashed lines represent carbon-carbon single bonds.

Inexpensive chemical compounds which can provide intense and long-lasting fruity and piney aromas with floral backgrounds are desirable in the art of perfumery. Many of the natural materials which provide such fragrances and contribute such desired nuances to perfumery compositions are high in cost, unobtainable at times, vary in quality from one batch to another and/or are generally subject to the usual variations of natural products.

There is, accordingly, a continuing effort to find synthetic materials which will replace, enhance or augment the fragrance notes provided by natural essential oils or compositions thereof. Unfortunately, many of the synthetic materials either have the desired nuances only to a relatively small degree, or they contribute undesirable or unwanted odor to the compositions.

Application for United States Letters Patent, Ser. No. 267,850 filed May 28, 1981 U.S. Pat. No. 4,359,412 entitled "Prins Reaction Products of Diisoamylene, Derivatives Thereof, Organoleptic Uses Thereof, and Processes for Preparing Same" discloses the perfumery uses of the Prins reaction product precursors of the mixture of aldehydes of the instant invention. Thus, Application for United States Letters Patent, Ser. No. 267,850, U.S. Pat. No. 4,359,412, describes the genus of compounds defined according to the structure:

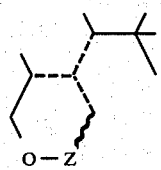

wherein one of the dashed lines represents a carbon-carbon double bond and each of the other of the dashed lines represent carbon-carbon single bonds; wherein the wavy line ∼∼∼ represents a carbon-carbon single bond or no bond; wherein when the wavy line represents a carbon-carbon single bond, Z represents methylene and when the wavy line represents no bond, Z represents hydrogen or $C_2$–$C_4$ alkanoyl, prepared according to the process of reacting at least one diisoamylene derivative defined according to the structure:

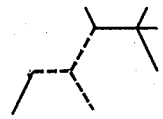

wherein one of the dashed lines represents a carbon-carbon double bond and each of the other of the dashed lines represent carbon-carbon single bonds or one of the structures:

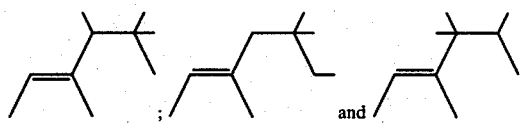

with formaldehyde or a formaldehyde source such as trioxane or paraformaldehyde in the presence of an alkanoic acid anhydride or an acid catalyst and then, optionally, hydrolyzing the resulting esters to form alcohols. The alcohols in that application are defined according to the structure:

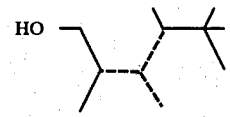

are indicated to have a woody, amber and floral aroma with minty and oriental-like nuances. The acetate esters which are precursors of the alcohols defined according to the structure:

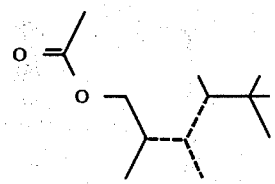

are indicated to have a woody, ionone-like, fruit and floral aroma with oriental nuances.

Application for United States Letters Patent, Ser. No. 233,861 filed on Feb. 12, 1981 U.S. Pat. No. 4,304,689, entitled "Aliphatic $C_{11}$ Branched Chain Aldehydes And Alcohols, Process For Preparing Same And Uses Thereof In Augmenting Or Enhancing The Aroma Of Perfumes, Colognes And/Or Perfumed Articles" discloses oxo reaction products of carbon monoxide and hydrogen with mixtures of diisoamylene or diisoamylene compounds. Thus, Application for United States Letters Patent, Ser. No. 233,861, U.S. Pat. No. 4,304,689, describes compounds defined according to the structure:

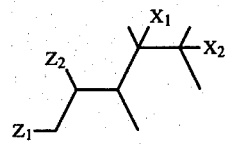

wherein one of $X_1$ or $X_2$ is hydrogen and the other of $X_1$ or $X_2$ is methyl; and wherein one of $Z_1$ or $Z_2$ is hydrogen and the other of $Z_1$ or $Z_2$ is hydroxymethyl having the structure:

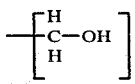

or carboxaldehyde having the structure:

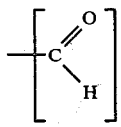

prepared by a process which comprises reacting at least one compound (a diisoamylene derivative) having a structure selected from the group consisting of:

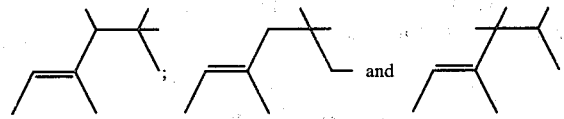

with a mixture of carbon monoxide and hydrogen at elevated temperatures and pressures thereby producing, as a general rule, a mixture of alcohols and aldehydes which are saturated. The perfumery use of the saturated aldehydes and alcohols is described in U.S. Pat. No. 4,304,689.

None of the reaction products of U.S. Pat. Nos. 4,304,689 or 4,359,412 has properties even remotely resembling the perfumery properties of the compounds of the instant invention. Indeed, the compounds of the instant invention have unexpected, unobvious and advantageous perfumery properties over the compounds described in U.S. Pat. No. 4,359,412 as well as for U.S. Pat. No. 4,304,689.

BRIEF DESCRIPTION OF THE DRAWINGS

FIG. AA represents the GLC profile for the reaction product of Example A using a 70% sulfuric acid catalyst at 35° C.

FIG. AB represents the GLC profile for the reaction product of Example A using an Amberlyst ® 15 acidic ion exchange resin catalyst at a temperature of 150° C.

FIG. AC represents the GLC profile for the reaction product of Example A using an Amberlyst ® 15 catalyst at 100° C.

FIG. AD represents the GLC profile for the reaction product of Example A using a sulfuric acid catalyst and an alpha-methyl styrene diluent at 35° C. according to the conditions of United Kingdom Patent Specification No. 796,130 (crude reaction product).

FIG. AE represents the GLC profile for the reaction product of Example A using a sulfuric acid catalyst at 35° C. and an alpha-methyl styrene diluent according to the conditions of United Kingdom Patent Specification No. 796,130 (distilled reaction product).

FIG. BA represents the NMR spectrum for peak 301 of the GLC profile of FIG. AE. Peak 301 has been determined by analysis to be the compound having the structure:

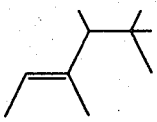

FIG. BB represents the infra-red spectrum for peak 301 of the GLC profile of FIG. AE.

FIG. CA represents the NMR spectrum for peak 302 of the GLC profile of FIG. AE. Peak 302 contains the compounds having the structures:

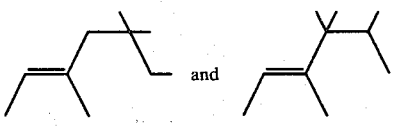

FIG. CB represents the infra-red spectrum for peak 302 of the GLC profile of FIG. AE.

FIG. D represents the NMR spectrum for peak 302 of the GLC profile of FIG. AB.

Figure 1:
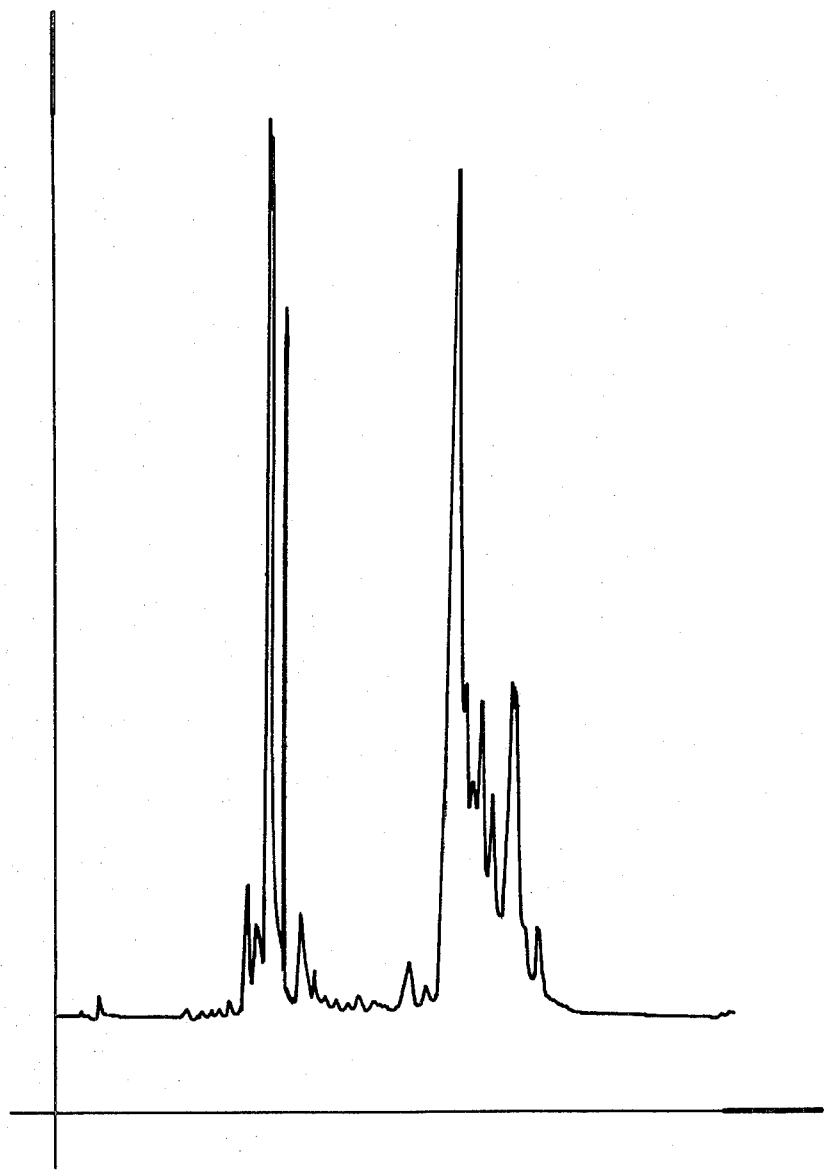

FIG. 1 is the GLC profile for the alcohol mixture produced according to Example I containing a mixture of compounds defined according to the structure:

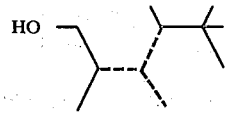

wherein in the mixture in each of the molecules one of the dashed lines represents a carbon-carbon double bond and each of the other of the dashed lines represent carbon-carbon single bonds.

Figure 2:
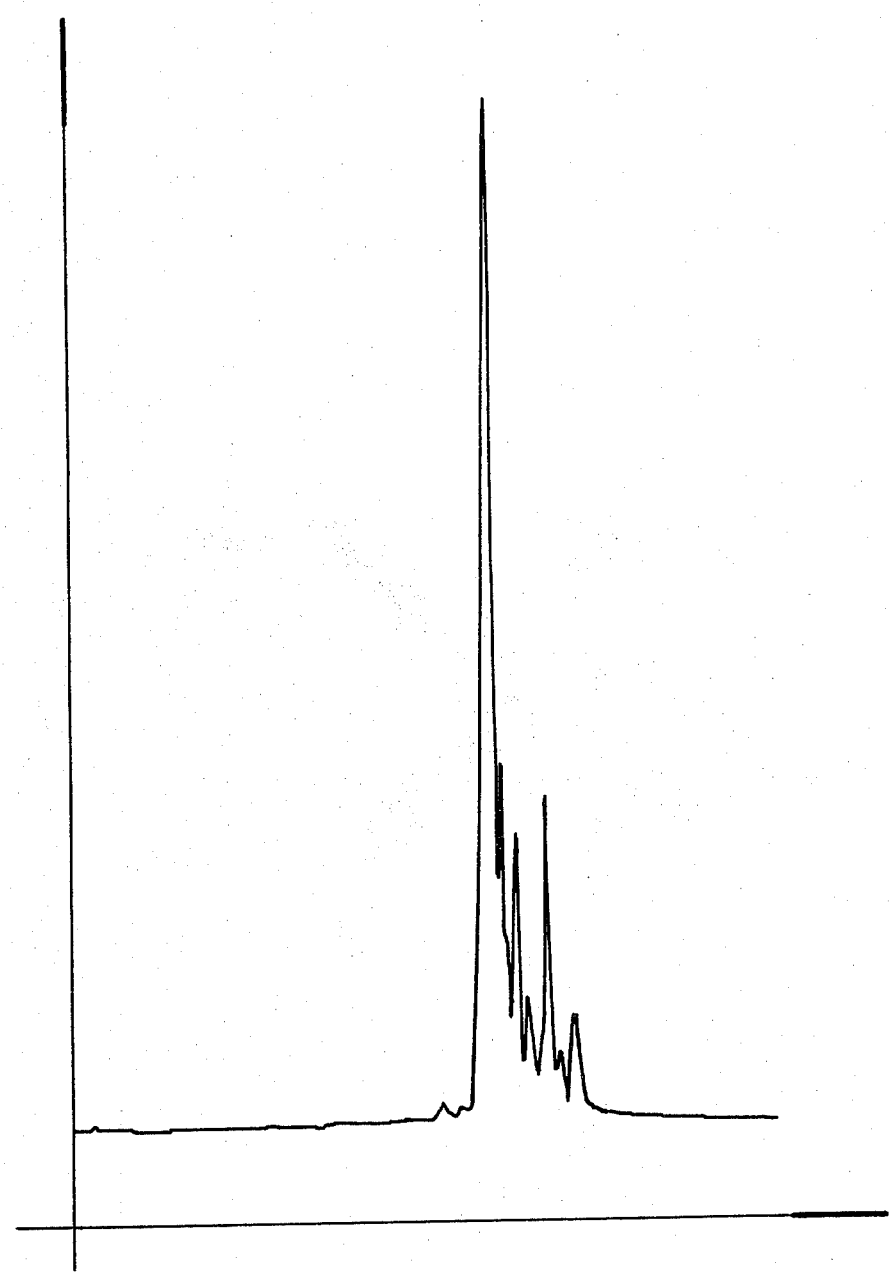

FIG. 2 is the GLC profile for bulked fractions 10–17 off the distillation product of the reaction product of Example I containing a mixture of compounds defined according to the structure:

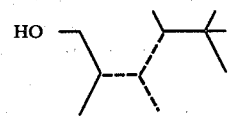

wherein in the mixture in each of the molecules one of the dashed lines represents a carbon-carbon double bond and each of the other of the dashed lines represent carbon-carbon single bonds.

Figure 3:
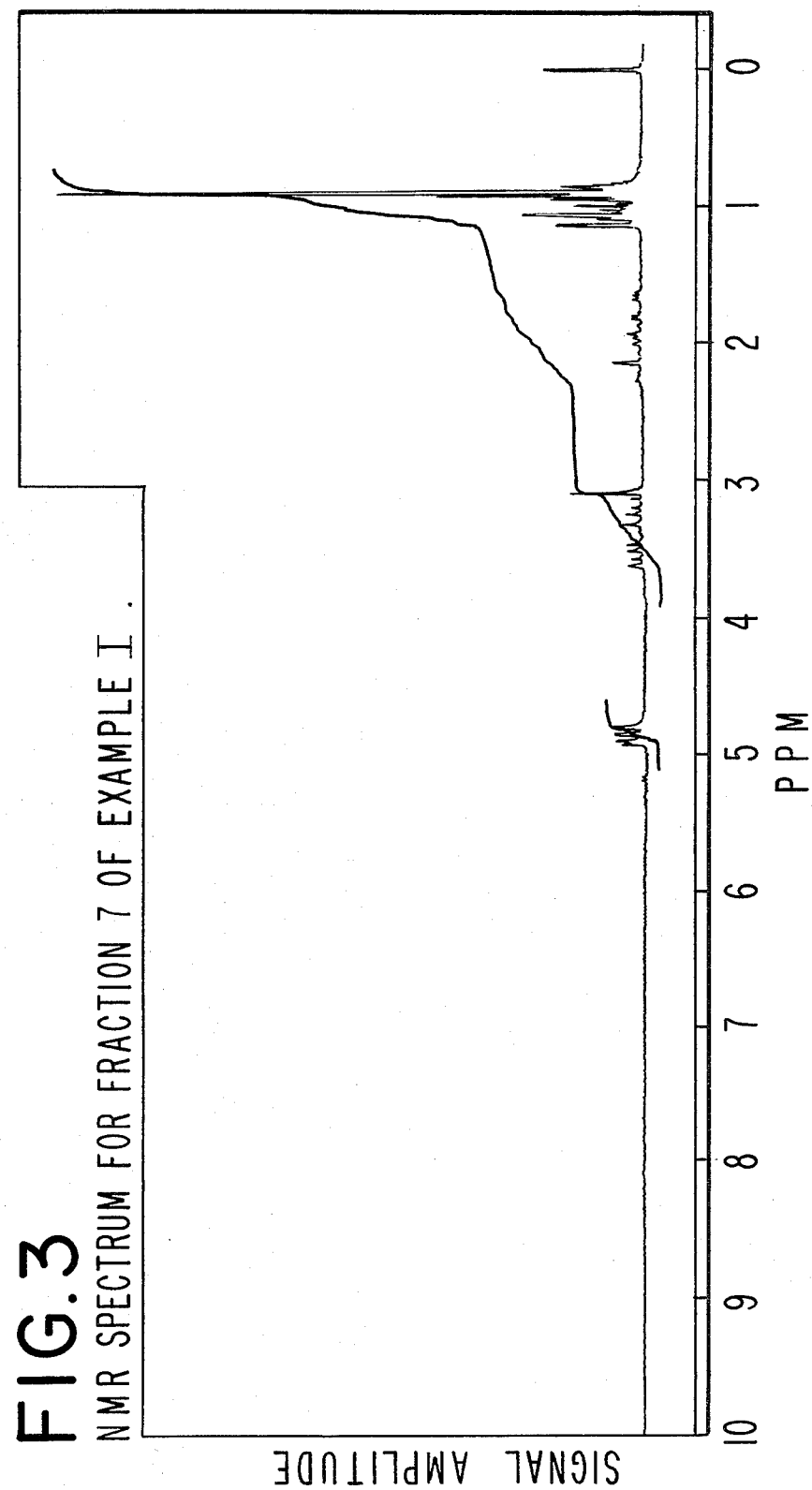

FIG. 3 is the NMR spectrum for fraction 7 of the distillation product of the reaction product of Example I containing a mixture of isomers defined according to the structure:

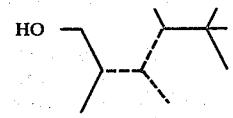

wherein in the mixture in each of the molecules one of the dashed lines represents a carbon-carbon double bond and each of the other of the dashed lines represent carbon-carbon single bonds.

Figure 4:
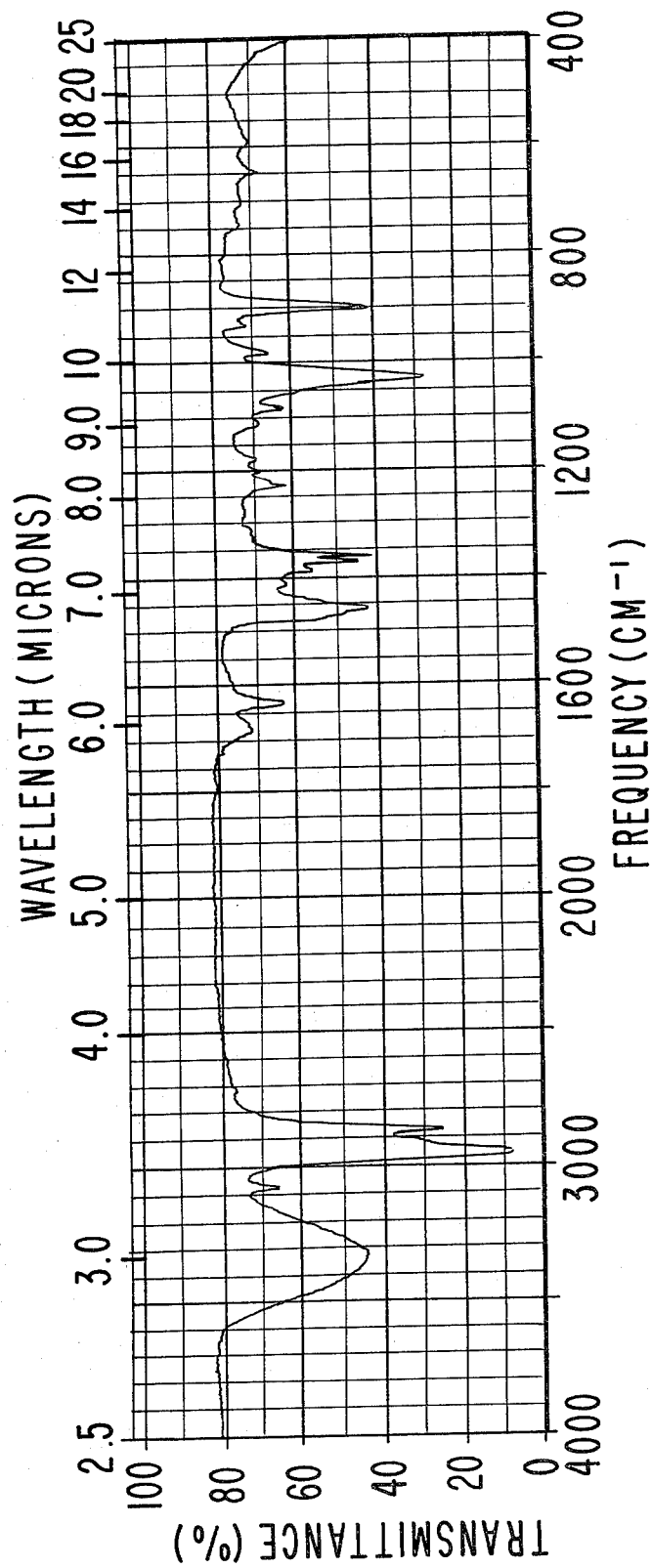

FIG. 4 is the infra-red spectrum for fraction 7 of the distillation product of the reaction product of Example I containing a mixture of compounds defined according to the structure:

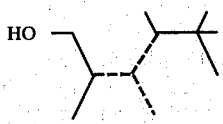

wherein in the mixture in each of the molecules one of the dashed lines represents a carbon-carbon double bond and each of the other of the dashed lines represent carbon-carbon single bonds.

Figure 5:
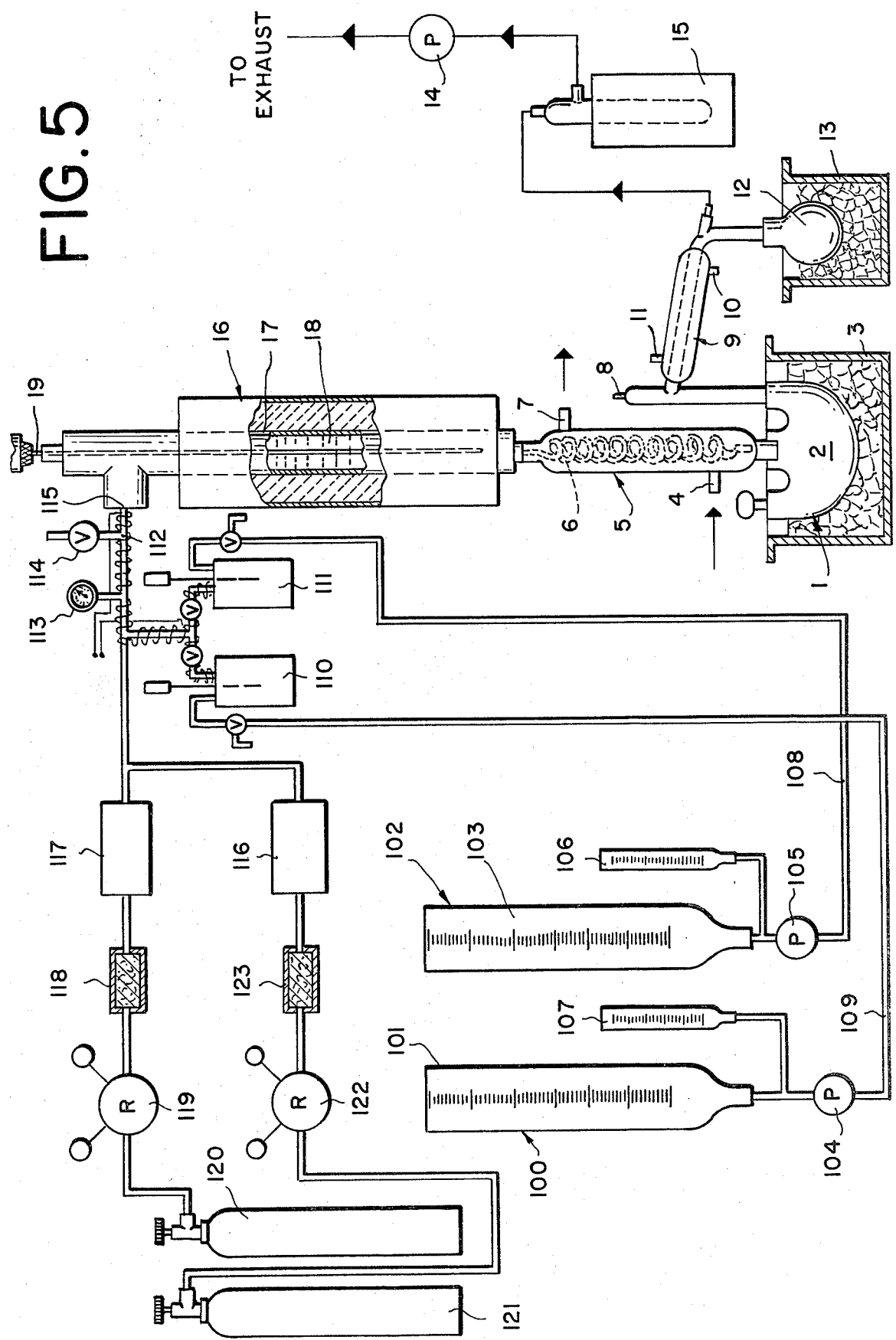

FIG. 5 is a schematic diagram of the apparatus used to carry out the oxidation reaction of Example II in order to effect the chemical reaction:

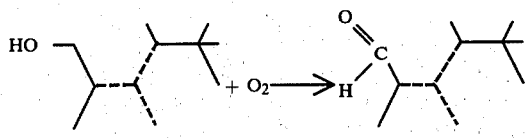

causing the production of a mixture of aldehydes by oxidizing a mixture of alcohols wherein in each of the mixtures in each of the molecules one of the dashed lines represents a carbon-carbon double bond and each of the other of the dashed lines represent carbon-carbon single bonds.

Figure 6:
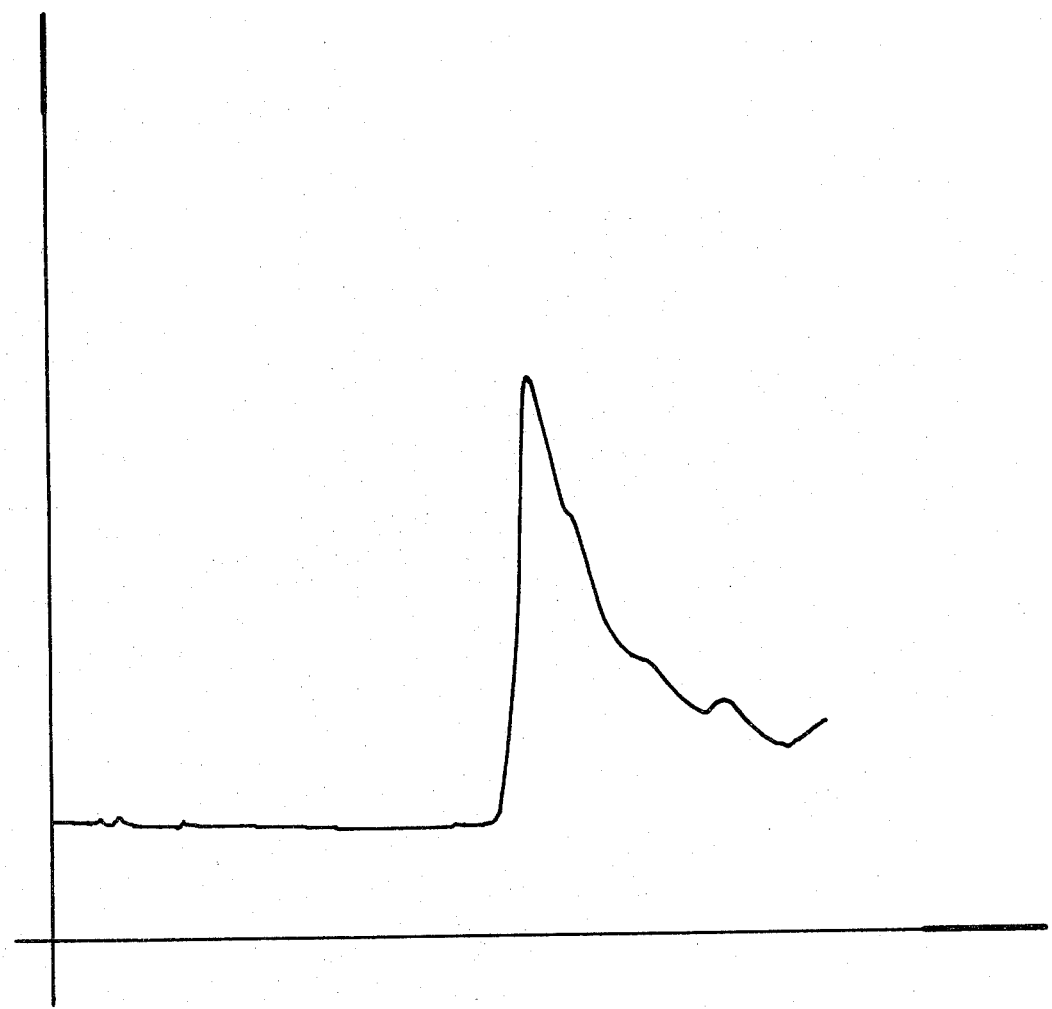

FIG. 6 is the GLC profile for the reactant used in Example II which is a mixture defined according to the structure:

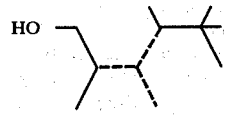

wherein in the mixture in each of the molecules one of the dashed lines represents a carbon-carbon double bond and each of the other of the dashed lines represent carbon-carbon single bonds.

Figure 7:
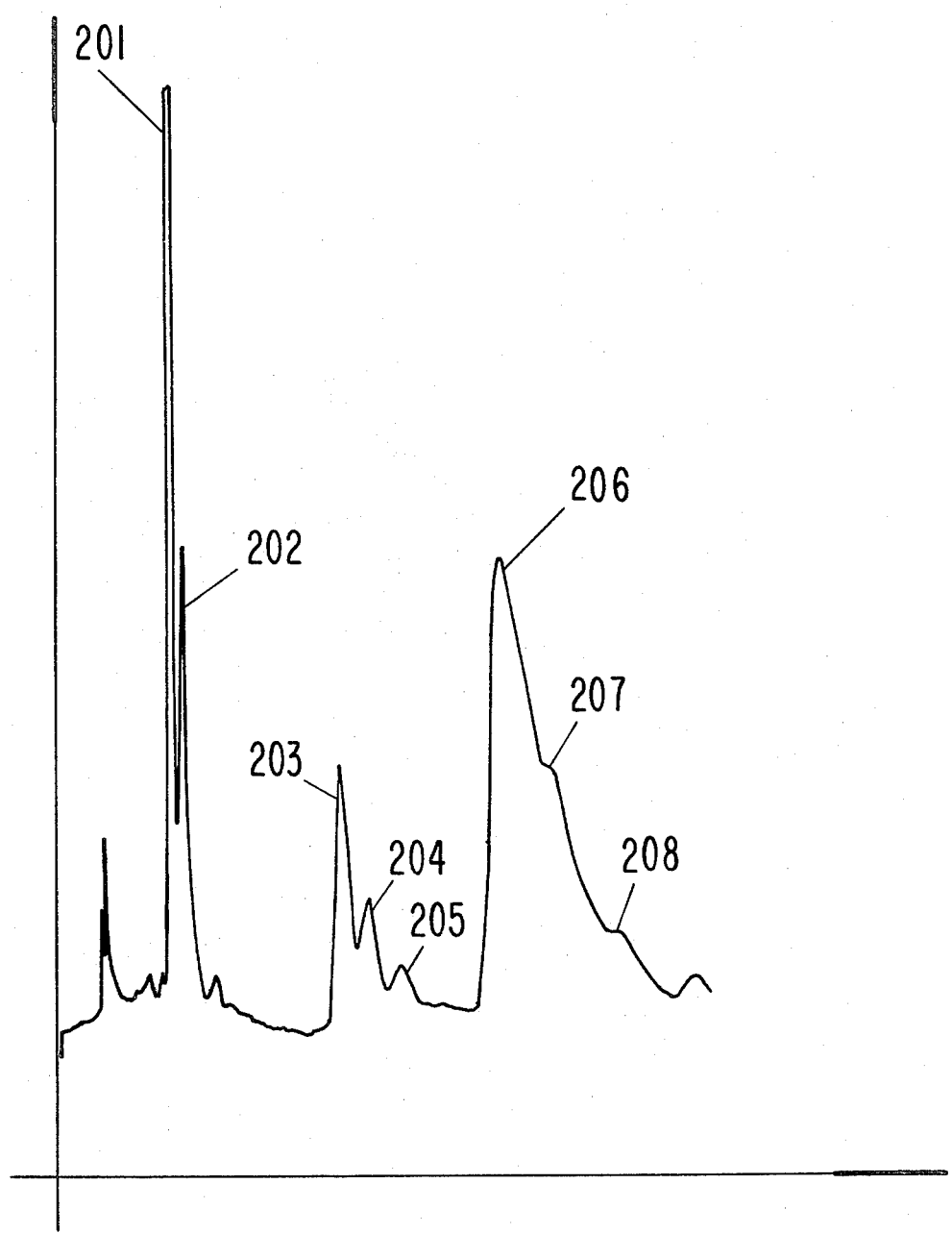

FIG. 7 is the GLC profile for the reaction product of Example II containing a major proportion of compounds defined according to the structure:

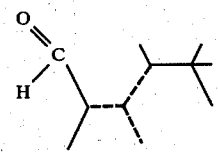

wherein in the mixture in each of the molecules one of the dashed lines represents a carbon-carbon double bond and each of the other of the dashed lines represent carbon-carbon single bonds.

FIG. 8 is the NMR spectrum for the reaction product of Example II containing a major proportion of a mixture of compounds defined according to the structure:

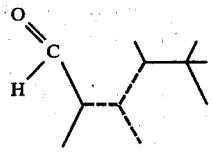

wherein in the mixture in each of the molecules one of the dashed lines represents a carbon-carbon double bond and each of the other of the dashed lines represent carbon-carbon single bonds.

FIG. 9 is the infra-red spectrum for the reaction product of Example II containing a major proportion of a mixture of compounds defined according to the structure:

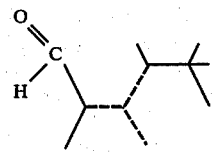

wherein in the mixture in each of the molecules one of the dashed lines represents a carbon-carbon double bond and each of the other of the dashed lines represent carbon-carbon single bonds.

DETAILED DESCRIPTION OF THE DRAWINGS

FIG. AE represents the GLC profile for the reaction product of Example A wherein a sulfuric acid catalyst catalyzes the dimerization of isoamylene to form diisoamylene in the presence of an alpha-methyl styrene diluent according to the conditions of United Kingdom Patent Specification 796,130. Peak 301 has been determined by analysis to be the compound having the structure:

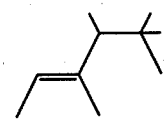

Peak 302 of the GLC profile contains the compounds having the structures:

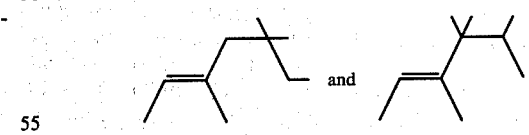

FIG. 5 represents a schematic diagram of the process equipment for carrying out the process of Example II for effecting the reaction:

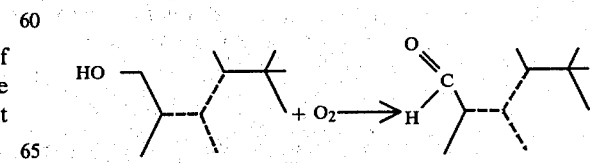

wherein a mixture of alcohols is oxidized over a silver catalyst to form a mixture of aldehydes wherein in each mixture in each of the molecules one of the dashed lines represents a carbon-carbon double bond and each of the other of the dashed lines represent carbon-carbon single bonds.

Organic reactant feed 100 which is the unsaturated alcohol mixture defined according to the structure:

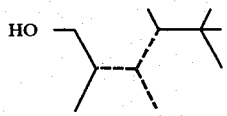

(wherein in the mixture in each of the molecules one of the dashed lines represents a carbon-carbon double bond and each of the other of the dashed lines represent carbon-carbon single bonds) further (Bulked Distillation Fractions 10-17 of the distillation product of the reaction product of Example I) held in holding tank 101 calibrated according to calibration apparatus 107 using pump 104 is fed through tube 109 simultaneously with water feed 103 held in holding tank 102 calibrated by calibration apparatus 106 (using pump 105 and tube 108 for the water feed) through vaporizers 110 (for the alcohol feed) and 111 (for the water feed) (wherein the mixture is heated) and then through heated tube 112 equipped with pressure gauge 113 and relief valve 114 into reaction tube 17 containing catalyst 18 (the reaction tube being heated using a cylindrical furnace 16 at 115). The catalyst bed 18 is rotated as a result of rotation of the rotatable rod 19. Simultaneously, air held in pressurized cylinder 120 under pressure and nitrogen held in pressurized cylinder 121 are pumped through regulator 119 (for the air) and regulator 122 (for the nitrogen) and filter 118 (for the air) and filter 123 (for the nitrogen) using mass flow controller 117 (for the air) and mass flow controller 116 (for the nitrogen) into heated tube 112 thereby creating a mixture of 112 of air, nitrogen, mixture of compounds defined according to the structure:

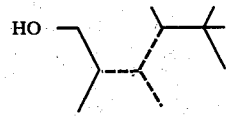

and water vapor. The reaction mixture passes through catalyst bed 18 through condensation coil 6 which is cooled using cooling water entering the heat exchanger 5 at location 4 and exiting at location 7. The condensed reaction product is retained in flask 2 at location 1, flask 2 being cooled using ice bath 3. Vacuum source 14 is used to assist the flow of the organic feed, the water feed, the nitrogen and the air or oxygen through reactor 17 into flask 2. Volatiles are condensed in flask 12 cooled by dry ice bath 13 and in the Dewar dry ice bath 15. Assisting in the cooling of the volatiles not retained in flask 2 is heat exchanger 9 wherein water is used as a coolant entering the heat exchanger at location 10 and exiting from the heat exchanger at location 11.

FIG. 7 is the GLC profile for the reaction product of Example II.

Peaks 201 and 202 represent low boiling by-products. Peaks 203, 204 and 205 represent reaction product containing a major proportion of mixture of compounds defined according to the structure:

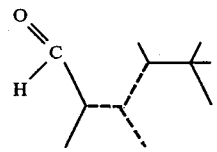

wherein in each of the molecules of the mixture one of the dashed lines represents a carbon-carbon double bond and each of the other of the dashed lines represent carbon-carbon single bonds.

Peaks 206, 207 and 208 represent the mixture of starting material reactants defined according to the structure:

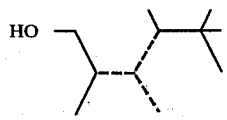

wherein in the mixture in each of the molecules one of the dashed lines represents a carbon-carbon double bond and each of the other of the dashed lines represent carbon-carbon single bonds.

THE INVENTION

The present invention provides a mixture containing a major proportion of compounds defined according to the structure:

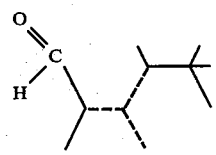

wherein in each of the molecules one of the dashed lines represents a carbon-carbon double bond and each of the other of the dashed lines represent carbon-carbon single bonds. More specifically the present invention provides substances containing a high proportion of compounds defined according tto the specific structures:

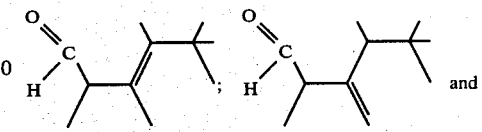

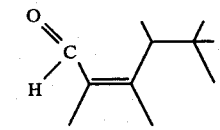

wherein the compounds having the structures:

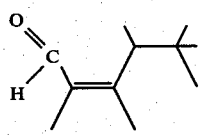 and 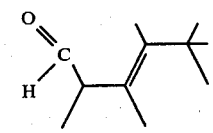

represent "cis" and/or "trans" isomers.

The composition of matter of our invention produced according to the process of our invention is capable of augmenting, enhancing or providing fruity, piney aromas with floral backgrounds in perfume compositions, colognes and perfumed articles (e.g., solid or liquid anionic, cationic, nonionic, zwitterionic detergents, fabric softener articles, drier-added fabric softener articles, cosmetic powders, hair preparations and the like).

The substances of our invention are produced by first reacting diisoamylene with formaldehyde or a formaldehyde precursor in the presence of or in the absence of an acyl anhdyride and in the presence of an acid catalyst. The resulting product (if an ester is formed) is then hydrolyzed to form the alcohol and the resulting alcohol is then oxidized using air or oxygen or a silver or copper chromite catalyst.

The unsaturated aldehyde compositions may be prepared by first reacting diisoamylene with formaldehyde or a formaldehyde precursor such as formalin or paraformaldehyde in the presence of or in the absence of an alkanoic acid anhydride and in the presence of an acid catalyst; either a Lewis acid such as boron trifluoride etherate or stannic chloride or the like, or a protonic acid such as sulfuric acid or phosphoric acid.

Depending on whether an acyl anhydride is used or not; and depending on whether a protonic acid or a Lewis acid catalyst is used; and depending upon whether formaldehyde or trioxane or paraformaldehyde is used as a precursor reactant, the resulting product encompassed within the generic structure:

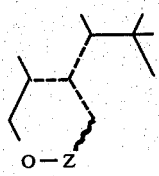

(wherein one of the dashed lines represents a carbon-carbon double bond and each of the other of the dashed lines represent carbon-carbon single bonds; wherein the wavy line ⁓ represents a carbon-carbon single bond or no bond; wherein when the wavy line represents a carbon-carbon single bond, Z represents methylene and when the wavy line represents no bond, Z represents hydrogen or $C_2$-$C_4$ acyl), will be different; that is, it will be either one of the compounds encompassed by the generic structure:

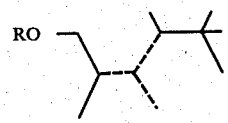

wherein R represents hydrogen or wherein R represents $C_2$-$C_4$ acryl or it will be one of the generic structures defined according to the structure:

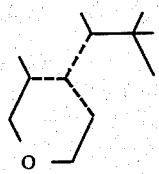

wherein one of the dashed lines represents a carbon-carbon double bond and wherein each of the other of the dashed lines represent carbon-carbon single bonds.

With respect to the diisoamylene precursor, "diisoamylene" is a dimer of isoamylene wherein the dimerization takes place in the presence of acid. "Diisoamylene" is indicated to be synthesized in the following references:

1 (i) Murphy & Lane, Ind. Eng. Chem., Prod. Res. Dev., Vol. 14, No. 3, 1975 p. 167 (Title: Oligomerization of 2-Methyl-2-Butene in Sulfuric Acid and Sulfuric-Phosphoric Acid Mixtures).

(ii) Whitmore & Mosher, Vol. 68, J. Am. Chem. Soc., February, 1946, p. 281 (Title: The Depolymerization of 3,4,5,5-Tetramethyl-2-hexene and 3,5,5-Trimethyl-2-heptene in Relation to the Dimerization of Isoamylenes).

(iii) Whitmore & Stahly, Vol. 67, J. Am. Chem. Soc., December, 1945, p. 2158 (Title: The Polymerization of Olefins. VIII The Depolymerization of Olefins in Relation to Intramolecular Rearrangements. II).

(iv) U.S. Pat. No. 3,627,700, issued on Dec. 14, 1971, (Zuech).

(v) U.S. Pat. No. 3,538,181, issued on Nov. 3, 1970 (Banks).

(vi) U.S. Pat. No. 3,461,184, issued on Aug. 12, 1969 (Hay, et al).

(vii) Gurwitsch, Chemische Berichte, 1912, Vol. 2, p. 796 (Production of Di-isoamylene from Isoamylene Using Mercury Acetate Catalyst). United Kingdom Pat. No. 796,130 published on June 4, 1958 discloses the synthesis of polyalkylindanes by means of, interalia, reacting alpha-methylstyrene with trimethylethene (2-methyl-butene-2) in the presence of an acid catalyst such as, sulfuric acid or boron trifluoride etherate. It is further indicated that such compounds are useful intermediates in the production of perfumery compounds. Apparently, however, the more volatile diisoamylenes produced as side-products in the reaction of 2-methyl-butene-2 with alphamethylstyrene have heretofore been discarded.

The "formaldehyde" precursor is shown as having the structure:

yet, in place of formaldehyde itself, trioxane having the structure:

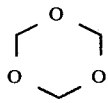

or paraformaldehyde having the structure:

HO⁺CH₂—O⁺ₓH wherein x is an integer of from 2 up to 40 may be used in place of formaldehyde. Whenever formaldehyde having the structure:

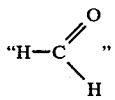

is shown in a reaction with quotation marks around it thusly:

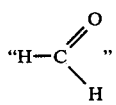

it is intended that this particular term mean either formaldehyde itself or trioxane or paraformaldehyde or formalin or any other form of formaldehyde.

When the reaction to produce the reaction products of our invention is carried out using paraformaldehyde as a precursor, and using a Lewis acid catalyst such as boron trifluoride etherate, stannic chloride, zinc chloride, zinc bromide, diethyl aluminum chloride, aluminum diethyl chloride, or the like, and in the presence of an acyl anhydride having the structure:

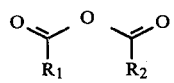

is produced, wherein $R_{12}$ represents $R_1$ or $R_2$ and one of the dashed lines in the resulting material is a carbon-carbon double bond and each of the other of the dashed lines are carbon-carbon single bonds.

When the reaction is carried out using formaldehyde per se, rather than paraformaldehyde, however, even in the presence of a Lewis acid catalyst such as stannic chloride or boron trifluoride etherate, and even in the presence of an acyl anhydride having the structure:

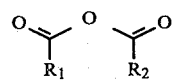

the compound that is formed is an alcohol or a mixture of alcohols defined according to the generic structure:

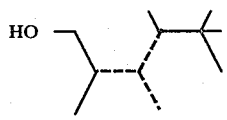

wherein one of the dashed lines represents a carbon-carbon double bond and each of the other of the dashed lines represent carbon-carbon single bonds.

When the reaction is carried out using formaldehyde alone, in the absence of an acyl anhydride, the reaction product is also the alcohol (or a mixture of alcohols) defined according to the structure:

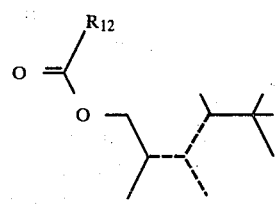

however, the alcohol at this particular point is formed in yields lower than that when compared to the reaction carried out first forming the ester having the structure:

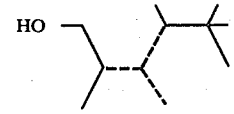

and then hydrolyzing this ester having the structure:

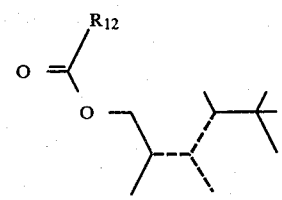

to form the alcohol having the structure:

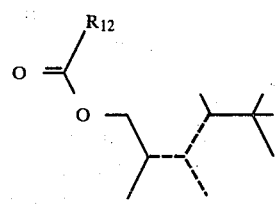

wherein in each of the molecules, one of the dashed lines represents a carbon-carbon double bond and each of the other of the dashed lines represent carbon-carbon single bonds.

Once the ester having the generic structure:

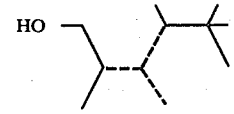

is formed, wherein $R_{12}$ represents $R_1$ and $R_2$ and each are the same or different and each represents $C_1$-$C_3$ alkyl, this material may be hydrolyzed in the presence of base to form, in relatively high yields, a mixture of compounds defined according to the structure:

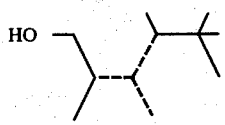

However, when using in place of a Lewis acid catalyst, a protonic acid catalyst such as sulfuric acid or phosphoric acid, even when using an acyl anhydride having the structure:

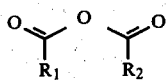

the reaction product, rather than having the structure:

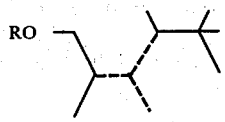

wherein R is hydrogen or $C_2$-$C_4$ acyl, is cyclic in nature having the structure:

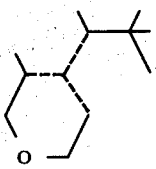

whereby 2 moles of formaldehyde react with 1 mole of diisoamylene to form such molecules having the structure:

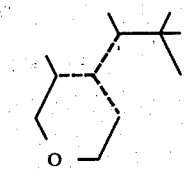

rather than the case where 1 mole of formaldehyde reacts as is the case in the presence of the Lewis acid catalyst forming the structure:

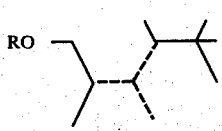

Where one of the compounds defined according to the structure:

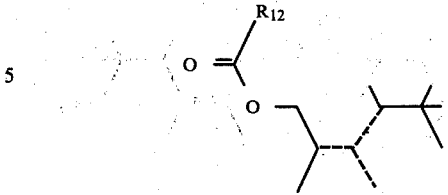

is formed wherein $R_{12}$ represents $C_1$-$C_3$ alkyl and one of the dashed lines represents a carbon-carbon double bond and the other of the dashed lines represent carbon-carbon single bonds, this compound is hydrolyzed in the presence of base to form one or a mixture of the compounds defined according to the genus:

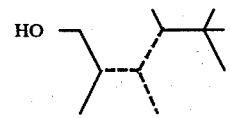

wherein one of the dashed lines represents a carbon-carbon double bond and the other of the dashed lines represent carbon-carbon single bonds.

The compounds defined according to the genus:

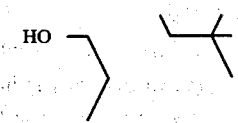

are then oxidized using either oxygen or air over a catalyst which is preferably a silver catalyst or a copper chromite catalyst according to the reaction:

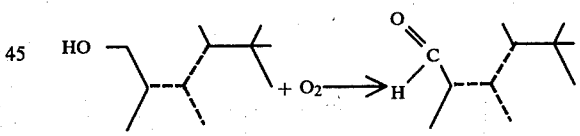

whereby the mixture of aldehydes defined according to the structure:

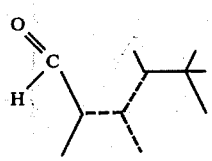

is formed, wherein in the mixture in each of the molecules one of the dashed lines represents a carbon-carbon double bond and each of the other of the dashed lines represent carbon-carbon single bonds. This mixture can be separated by the usual chromatographic techniques such as high pressure liquid chromatography to form the compounds having the structures:

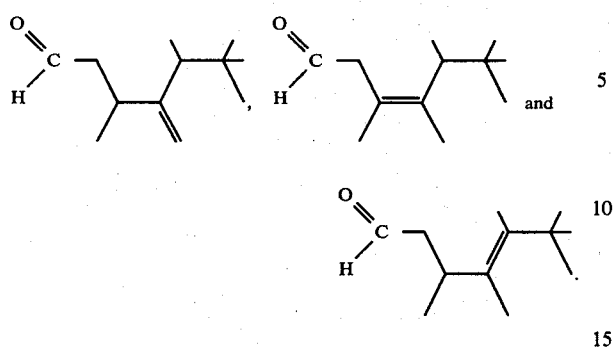

From a commerical standpoint, however, the mixture containing a high proportion of compounds defined according to the structure:

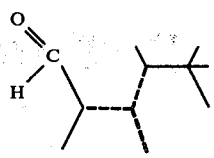

is all that is necessary to form a desirable perfume adjuvant.

Thus, the reaction sequences encompassed by our invention are as follows:

(a) The reaction of the alkanoic acid anhydride with diisoamylene and formaldehyde in the presence of a Lewis acid catalyst to form the $C_{11}$ alcohol ester thusly:

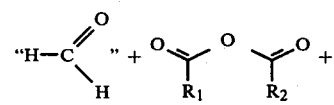

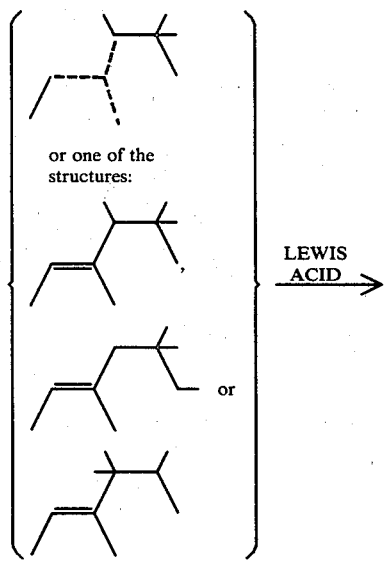

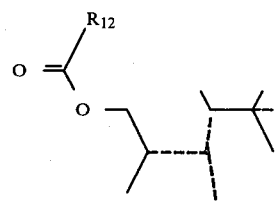

wherein $R_1$ and $R_2$ are the same or different and each represents $C_1$–$C_3$ alkyl; wherein $R_{12}$ is $R_1$ or $R_2$ and represents $C_1$–$C_3$ alkyl and wherein one of the dashed lines represents a carbon-carbon double bond and each of the other of the dashed lines represent carbon-carbon single bonds;

(b) The hydrolysis reaction:

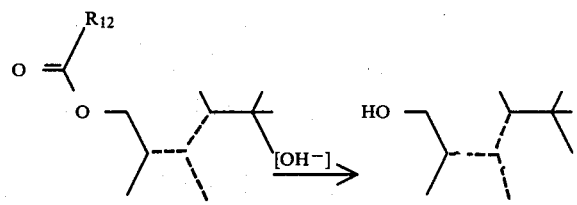

wherein $R_{12}$ and the dashed lines are defined as above; and (c) The oxidation reaction:

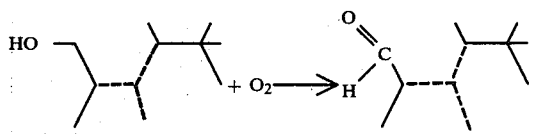

wherein one of the dashed lines represents a carbon-carbon double bond and the other of the dashed lines represent carbon-carbon single bonds.

In the esterification reaction:

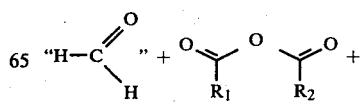

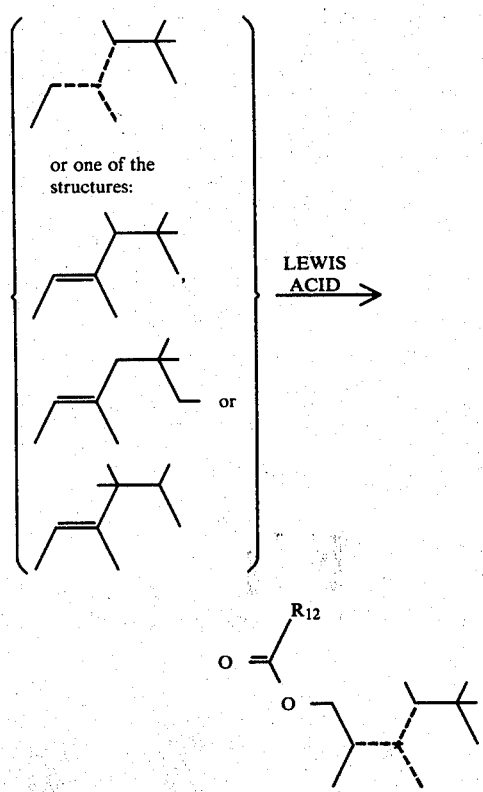

the Lewis acid may be borontrifluoride etherate, stannic chloride, zinc chloride, zinc bromide, ethyl aluminum dichloride, diethyl aluminum chloride, or aluminum trichloride. $R_1$ and $R_2$ may be the same or different and each represents $C_1$-$C_3$ alkyl such as methyl, ethyl, isopropyl or n-propyl. The formaldehyde used may be and is preferably paraformaldehyde, however, trioxane may also be used. Formaldehyde itself or formalin should not be used if the ester is attempted to be formed since low yields of alcohol will be formed rather than the ester in accordance with the reaction:

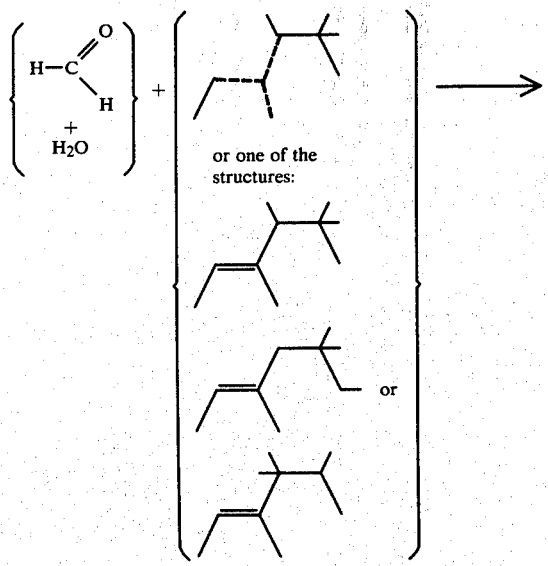

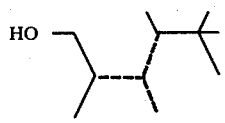

Trioxane has the structure:

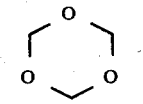

Paraformaldehyde is indicated by the structure:

$$HO+CH_2-O+_xH$$

The mole ratio of diisoamylene:formaldehyde (as paraformaldehyde or as trioxane) may vary from about 1:2 up to about 2:1 with a preferred mole ratio of about 1:1. The mole ratio of acyl anhydride:diisoamylene may vary from about 1:1 up to about 2:1 acyl anhydride:diisoamylene with a preferred mole ratio of 1.4–1.5:1 of acyl anhydride:diisoamylene. The concentration of diisoamylene in the reaction mass is preferably from about 1 mole per liter up to about 5 moles per liter.

The concentration of Lewis acid in the reaction mass may vary from about 0.01 moles per liter up to about 0.5 moles per liter.

The reaction temperature may vary from about 50° C. up to about 150° C. depending on the pressure above the reaction mass and depending upon the time desired to complete the reaction for a given particular yield. When higher temperatures are used, the time of reaction required for completion is shorter, however, the yield is lower and the quality of by-product formed is greater. The most desirable reaction temperature varies between 80° and 110° C. It is most preferable to carry out the reaction at atmospheric pressure. Higher reaction pressures or lower reaction pressures do not give rise to a higher yield or higher conversion rate.

At the end of the reaction, the reaction mass may be "worked-up" in the usual way by means of, for example, distillation or chromatographic separation, e.g. commercial high-pressure liquid chromatography.

In carrying out the hydrolysis reaction to form the $C_{11}$ unsaturated alcohol thusly:

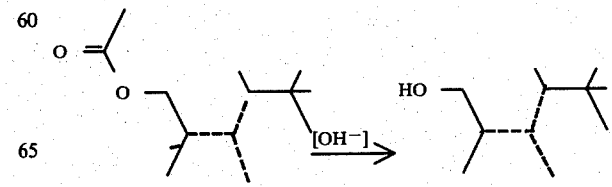

the mole ratio of ester having the structure:

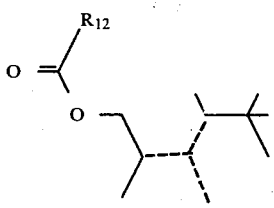

to alkali metal hydroxide, e.g., potassium hydroxide, sodium hydroxide or lithium hydroxide, may vary from about 1:2 up to about 2:1 with an excess of alkali metal hydroxide being preferred. That is, it is preferred that the mole ratio of alkali metal hydroxide:ester having the structure:

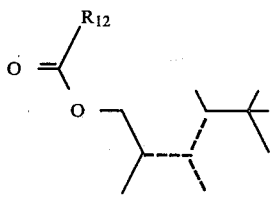

be about 2:1. It is preferred that the hydrolysis reaction to form the compound having the structure:

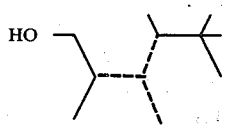

be carried out using highly concentrated base, e.g., from about 30% up to about 50% concentration. Concentration of ester having the structure:

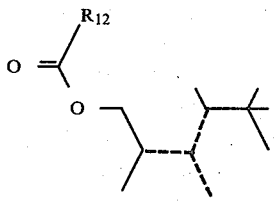

in the reaction mass may vary from about 2 moles per liter up to about 8 moles per liter with a concentration of 2–3 moles per liter of ester having the structure:

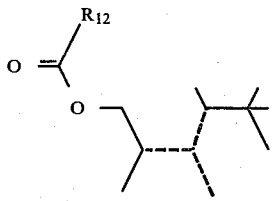

being preferred. The concentration of caustic is preferably double the concentration of ester. Thus, the concentration of caustic may vary from about 3 moles per liter up to about 10 moles per liter with a preferred concentration of caustic being about 5 moles per liter. The temperature of hydrolysis is preferably between about 50° C. up to about 80° C. with a hydrolysis temperature of 65° C. being preferred, at atmospheric pressure. Pressures above atmospheric pressure or below atmospheric pressure may be used for the hydrolysis reaction but using higher or lower pressures does not give rise to any advantage insofar as yield or conversion per unit time is concerned. Indeed, most economically, the reaction pressure for this hydrolysis reaction is preferably 1 atmosphere.

At the end of the hydrolysis reaction, the reaction mass may be appropriately worked up as by pH adjustment and fractional distillation thereby yielding the $C_{11}$ unsaturated alcohol or mixtures defined according to the structure:

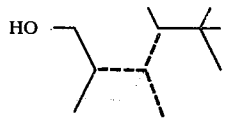

wherein one of the dashed lines represents a carbon-carbon double bond and each of the other of the dashed lines represent carbon-carbon single bonds.

The oxidation or reaction to form the aldehyde:

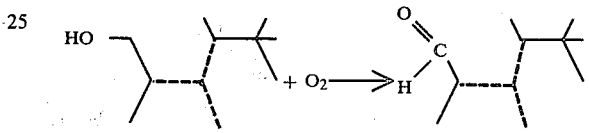

is preferably carried out in apparatus described in the "Detailed Description of The Drawings" section of the instant specification, supra, and schematically shown in FIG. 5. The oxidation may use either air or oxygen. The oxidation catalyst may either be silver or copper chromite ($CuCrO_3$).

The reaction temperature may vary from 200° C. up to 500° C. but the temperature is dependent upon the desired yield and required residence time of the mixture of compounds defined according to the structure:

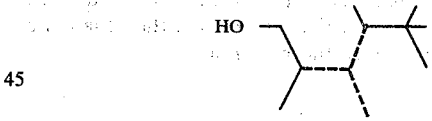

in contact with the solid catalyst. Necessarily, the reaction is vapor phase and the surface area of catalyst and flow rate of reactants as well as residence time and reaction temperature and pressure are all important variables which must be optimized in relation to one another if yield and conversion of product are to be optimized. It is preferred that the reaction be carried out in the presence of water vapor and it is also preferred that the water flow rate and flow rate of alcohol reactant be approximately equal. The gas flow rates may vary between 50 and 400 ml per minute with a preferred oxygen flow rate of 285 ml per minute at a temperature of reaction of 450° C.; a liquid alcohol flow rate of 2 ml per minute and water flow rate of 2 ml per minute. As will be seen by an examination of FIG. 7, (the GLC profile of the reaction product of Example II) the yield using the foregoing conditions is approximately 60%. Separation of the aldehyde reaction product from the alcohol reactant and recycling of the alcohol reactant will, of course, raise the yield. A higher temperature of reaction, e.g., 500° C. and longer residence time (e.g., greater distance of travel of reactant through catalyst and/or area of contact with catalyst) will raise the yield to approximately 80%, the higher residence time being approximately 20% greater than what is used in Example II.

One or more unsaturated aldehyde compositions prepared in accordance with the process of our invention and one or more auxiliary perfume ingredients including, for example, alcohols, aldehydes other than the unsaturated aldehydes of our invention, ketones, terpenic hydrocarbons, nitriles, esters, lactones, natural essential oils and synthetic essentential oils may be admixed so that the combined odors of the individual components produce a pleasant and desired fragrance particularly and preferably in the pine, floral and "chypre" fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all states of evaporation and substances which retard evaporation; and (d) topnotes which are usually low-boiling fresh-smelling materials.

In perfume compositions, it is the individual components which contribute their particular olfactory characteristics, however, the overall sensory effect of the perfume composition will be at least the sum total of the effects of each of the ingredients. Thus, the unsaturated aldehyde compositions prepared in accordance with the process of our invention can be used to alter, modify, or enhance the aroma characteristics of a perfume composition, for example, by utilizing or moderating the olfactory reaction contributed by another ingredient in the composition.

The amount of the unsaturated aldehyde compositions prepared in accordance with the process of our invention which will be effective in perfume compositions as well as in perfumed articles (e.g., anionic, non-ionic, cationic or zwitterionic detergents, soaps and fabric softener compositions and articles) and colognes depends upon many factors including the other ingredients, their amounts and the effects which are desired. It has been found that perfume compositions containing as little as 0.01% of the unsaturated aldehyde compositions prepared in accordance with the process of our invention or even less (e.g., 0.005%) can be used to impart a fruity and piney aroma with a floral background to soaps, cosmetics, anionic, cationic, nonionic or zwitterionic detergents, fabric softener compositions, fabric softener articles, microporous polymers, particularly polyacrylic resins or other products. The amount employed can range up to 70% of the fragrance components and will depend on considerations of cost, nature of the end product, the effect desired on the finished product and the particular fragrance sought.

The unsaturated aldehyde compositions prepared in accordance with the process of our invention are useful (taken alone or taken together with other ingredients in perfume compositions) as (an) olfactory component(s) in detergents and soaps, space odorants and deodorants, perfumes, colognes, toilet water, bath preparations, such as creams, deodorants, hand lotions and sun screens; powders, such as talcs, dusting powders, face powders microporous "perfumed" slow release polymers and the like. When used as (an) olfactory component(s) in perfumed articles as little as 0.05% of the unsaturated aldehyde compositions prepared in accordance with the process of our invention, will suffice to impart, augment or enhance a fruity, piney aroma with a floral background to perfumed articles which have pine or "chypre" type aromas. Generally, no more than 6% of the unsaturated aldehyde compositions of our invention based on the ultimate end product is required in the perfumed article.

In addition, the perfume composition or fragrance composition of our invention can contain a vehicle or carrier for the unsaturated aldehyde compositions prepared in accordance with the process of our invention. The vehicle can be a liquid, such as non-toxic alcohol, a non-toxic glycol, or the like. The carrier can also be an absorbent solid, such as a gum (e.g., gum arabic) or components for encapsulating the composition (such as gelatin) as by coacervation or polymers such as urea formaldehyde polymers.

It will thus be apparent that the unsaturated aldehyde compositions prepared in accordance with the process of our invention can be utilized to alter, modify or enhance sensory properties, particularly organoleptic properties such as fragrances of a wide variety of consumable materials.

The following Examples A and I set forth means for synthesizing precursors for use in synthesizing the products of our invention. The following Example II illustrates a method of our invention used to manufacture the unsaturated aldehyde compositions of our invention. Examples subsequent to Example II serve to illustrate the organoleptic utilities of the unsaturated aldehyde compositions of our invention (the unsaturated aldehydes being manufactures in accordance with the process of Example II or an equivalent thereof).

All parts and percentages given herein are by weight unless otherwise specified.

EXAMPLE A

PREPARATION OF DIISOAMYLENE

Reaction:

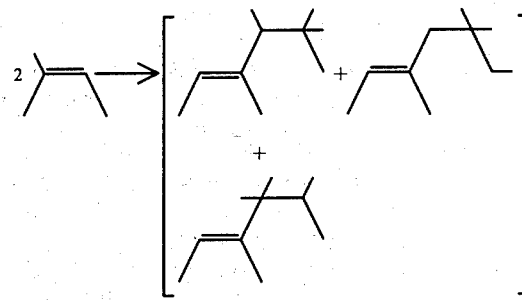

Diisoamylene is prepared according to one of the procedures set forth in the following references:

(i) Murphy & Lane, Ind. Eng. Chem., Prod. Res. Dev., Vol. 14, No. 3, 1975 p. 167 (Title: Oligomerization of 2-Methyl-2-Butene in Sulfuric Acid and Sulfuric-Phosphoric Acid Mixtures).

(ii) Whitmore & Mosher, Vol. 68, J. Am. Chem. Soc., February, 1946, p. 281 (Title: The Depolymerization of 3,4,5,5-Tetramethyl-2-hexene and 3,5,5,-Trimethyl-2-heptene in Relation to the Dimerization of Isoamylenes).

(iii) Whitmore & Stahly, Vol. 67, J. Am. Chem. Soc., December, 1945, p. 2158 (Title: The Polymerization of Olefins. VIII The Polymerization of Olefins in Relation to Intramolecular Rearrangements. II).
(iv) U.S. Pat. No. 3,627,700 issued on Dec. 14, 1971, (Zuech).
(v) U.S. Pat. No. 3,538,181 issued on Nov. 3, 1970, (Banks).
(vi) U.S. Pat. No. 3,461,184 issued on Aug. 12, 1969 (Hay, et al).
(vii) Gurwitsch, Chemische Berichte, 1912, Vol. 2, p. 796 (Production of Di-isoamylene From Isoamylene Using Mercury Acetate Catalyst).

As an illustration, and not by way of limitation, the following example sets forth the preparation of diisoamylenes useful in producing the fragrance materials of our invention.

Over a period of ten hours, 2-methyl-2-butene is pumped through a 5'×⅜ (0.625 inch) tube packed with 15.0 grams of polystyrene sulfonic acid catalyst, at a temperature of 100° C. and at a pressure of 400 psig.

The resulting material was distilled in a fractionation column in order to separate the diisoamylene from the higher molecular weight polymers, which are formed during the reaction as by-products. This material distills at 36'-40' C. vapor temperature; 74°-94° C. liquid temperature and 4-5 mm Hg pressure.

FIG. AA represents the GLC profile for the reaction product of this Example A using a 70% sulfuric acid catalyst at 35° C.

FIG. AB represents the GLC profile for the reaction product of this Example A using an Amberlyst®15 acidic ion exchange resin catalyst at a temperature of 150° C.

FIG. AC represents the GLC profile for the reaction product of this Example A, using an Amberlyst®15 catalyst at 100° C.

FIG. AD represents the GLC profile for the reaction product of this Example A, using a sulfuric acid catalyst and an alpha-methylstyrene diluent at 35° C. according to the conditions of United Kingdom Patent Specification No. 796,130 (crude reaction product).

FIG. AE represents the GLC profile for the reaction product of this Example A, using a sulfuric acid catalyst at 35° C. and an alpha-methylstyrene diluent according to the conditions of United Kingdom Patent Specification 796,130 (distilled reaction product). Distillation range: 36°-40° C. vapor temperature; 74°-94° C. liquid temperature and 4-5 mm HG pressure.

FIG. BA represents the NMR spectrum for peak 301 of the GLC profile of FIG. AE. Peak 301 has been determined by analysis to be the compound having the structure:

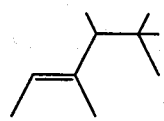

FIG. BB represents the infra-red spectrum for peak 301 of the GLC profile of FIG. AE.

FIG. CA represents the NMR spectrum for peak 302 GLC profile of FIG. AE. Peak 302 contains the compounds having the structures:

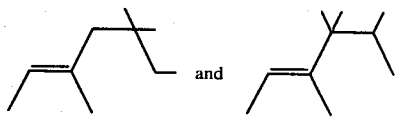

FIG. CB represents the infra-red spectrum for peak 302 of the GLC profile of FIG. AE.

FIG. D represents the NMR spectrum for peak 302 of the GLC profile of FIG. AB.

EXAMPLE I

Reaction:

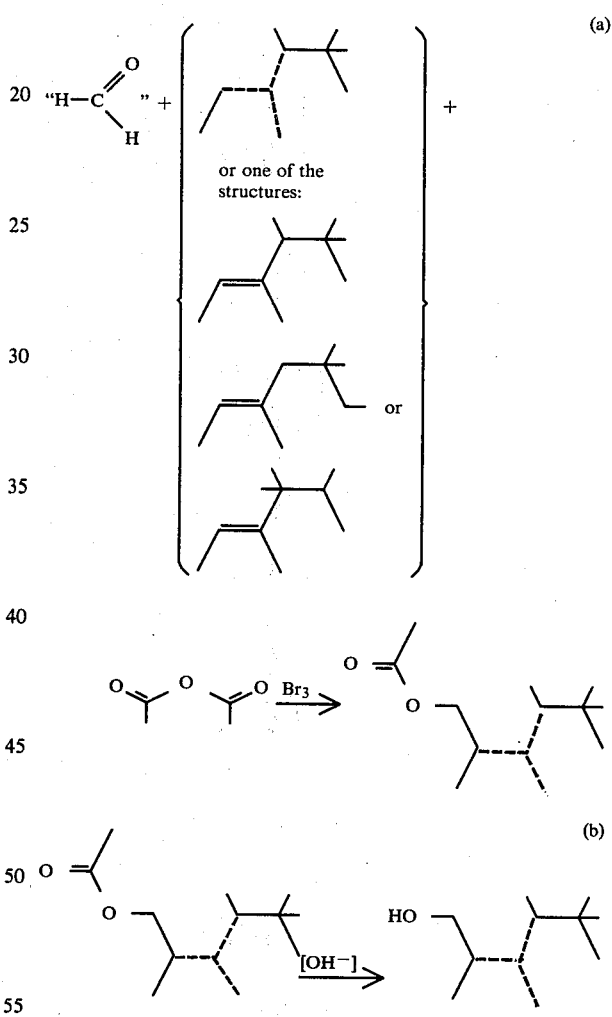

Into a 12 liter flask equipped with stirrer, condenser, thermometer, heating mantle and addition funnel is placed a mixture of 40 grams of boron trifluoride diethyl etherate, and 1400 grams of acetic anhydride. The resulting mixture is heated to 90° C. A slurry of 2000 grams of the diisoamylene prepared according to Example A (distilling at 36°-40° C. vapor temperature; 74°-94° C. liquid temperature and 4-5 mm Hg pressure) and 430 grams of paraformaldehyde is then prepared. While maintaining the reaction mass temperature at 90° C. over a period of 3 hours the resulting slurry is slowly fed to the reaction mass. At the end of the 3 hour period one liter of water is then added over a period of 30 minutes while maintaining the reaction mass at 90° C.

The resulting reaction mass is poured into two liters of 10% sodium chloride solution. The resulting product now exists in two phases; an organic phase and an aqueous phase. The organic phase is then returned to the 12 liter flask and admixed with one liter of 50% sodium hydroxide and 10 grams of Aliquat ®336 (Registered Trademark of the General Mills Chemical Company of Minneapolis, Minnesota, identifying Tricapryl Methyl Ammonium Chloride). The resulting mixture is heated to 50° C. and 200 ml water is then added. The resulting mixture is agitated at 50° C. for a period of 2 hours. The resulting product is then cooled to room temperature and poured into 2 liters of water. The aqueous layer is removed and the organic layer is neutralized to a pH of between 6 and 7. The organic layer is then distilled on a 12 inch silver Goodloe column yielding the following fractions:

| Fraction No. | Vapor Temp. | Liquid Temp. | Vacuum (mm Hg Pressure) | Reflux Ratio | Wgt. of Fraction |
| --- | --- | --- | --- | --- | --- |
| 1 | 25/32 | 87/90 | 3.0/3.0 | 9:1 | 17.2 |
| 2 | 52 | 85 | 3.0 | 9:1 | 17.4 |
| 3 | 60 | 90 | 3.0 | 9:1 | 13.4 |
| 4 | 65 | 94 | 3.0 | 9:1 | 15.8 |
| 5 | 65 | 94 | 3.0 | 9:1 | 22.4 |
| 6 | 65 | 94 | 3.0 | 9:1 | 19.0 |
| 7 | 68 | 95 | 3.0 | 4:1 | 73.3 |
| 8 | 68 | 95 | 3.0 | 4:1 | 86.2 |
| 9 | 68 | 95 | 3.0 | 4:1 | 94.3 |
| 10 | 68 | 95 | 3.0 | 4:1 | 86.7 |
| 11 | 68 | 95 | 3.0 | 4:1 | 88.0 |
| 12 | 68 | 95 | 3.0 | 4:1 | 91.7 |
| 13 | 70/72 | 97/97 | 3.0/3.0 | 4:1 | 73.0 |
| 14 | 72 | 95 | 3.0 | 4:1 | 51.2 |
| 15 | 74 | 96 | 3.0 | 4:1 | 83.0 |
| 16 | 75 | 97 | 3.2 | 4:1 | 94.9 |
| 17 | 76 | 97 | 3.0 | 4:1 | 93.0 |
| 18 | 95 | 108 | 6.0 | — | 72.1 |
| 19 | 78 | 109 | 2.8 | 4:1 | 78.7 |
| 20 | 80 | 145 | 2.5 | 4:1 | 65.6 |
| 21 | 82 | 170 | 1.8 | 4:1 | 6.3 |

Fractions 10-17 are bulked for utilization in Example II.

FIG. 1 is the GLC profile for the reaction product prior to distillation (conditions: 10'×¼" SE-30 column programmed at 130° C., isothermal).

FIG. 2 is the GLC profile for bulked fractions 10-17 of the foregoing distillation (conditions: 10'×¼" SE-30 column, programmed at 130° C.; isothermal).

FIG. 3 is the NMR spectrum for fraction 3 of the foregoing distillation containing a major proportion of isomers defined according to the structure:

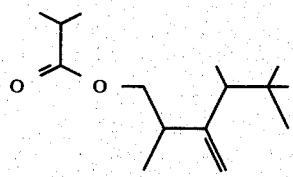

wherein in each of the molecules one of the dashed lines represents a carbon-carbon double bond and each of the other of the dashed lines represent carbon-carbon single bonds.

FIG. 4 is the infra-red spectrum for fraction 7 of the foregoing distillation containing a major proportion of isomers defined according to the structure:

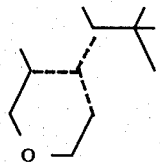

wherein in each of the molecules one of the dashed lines represents a carbon-carbon double bond and each of the other of the isomers represent carbon-carbon single bonds.

EXAMPLE II

PREPARATION OF UNSATURED ALDEHYDE

Reaction:

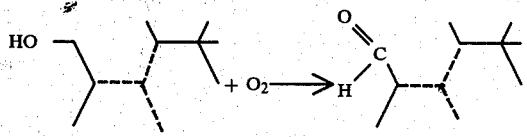

Using the apparatus of FIG. 5, a catalytic oxidation of the alcohol mixture (bulked fractions 10-17) produced according to Example I is carried out. Maintaining the silver catalyst and reaction tube at a temperature of 450° C. (using furnace 16 and silver catalyst 18 on shaft 19 in reactor 17, oxygen held in vessel 120 is permitted to flow at a flow rate of 285 ml per minute through regulator 119, filter 118 and mass flow controller 117 through heater 112 while at the same time nitrogen at a flow rate of 100 ml per minute is permitted to flow through regulator 122, filter 123 and mass flow controller 116 whereupon the nitrogen flow joins the oxygen flow and the combined gases (the nitrogen, oxygen and alcohol mixture) are fed through heater 112 into reactor 17. Simultaneously, the bulked fractions 10-17 of the distillation product of the alcohol-containing reaction product 100, held in holding tank 101 is pumped through pump 104 into vaporizer 110 through heating tube 112 along with the oxygen and nitrogen. Simultaneously, water 103 held in holding tank 102 is pumped through pump 105 through tube 108 into vaporizer 111 and finally through heated tube 112 along with the oxygen, nitrogen and the alcohol reactant, (bulked fractions 10-17 of the distillation product of the reaction product produced according to Example I) and finally into the reactor 17 and the silver catalyst 18 at 450° C. The flow rate of the bulked fractions 10-17 containing a major proportion of compounds defined according to the structure:

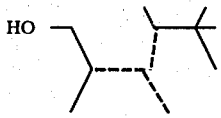

is 2 ml per minute (liquid). The liquid flow rate of the water is also 2 ml per minute.

The reaction product is condensed in heat exchanger 5 at 6 and is collected at location 1 in flask 2 which is cooled by ice-bath 3. Volatiles are collected in flask 12 and cooled by dry ice bath 13. A vacuum 14 is applied wherein the final volatiles are not permitted to escape but are collected at 15.

The detailed description of FIG. 5 is set forth in the section entitled "Detailed Description of the Drawings", supra.

FIG. 6 is the GLC profile of the starting material, bulked fractions 10-17 of the distillation product of the reaction product of Example I.

FIG. 7 is the GLC profile for the reaction product of this example (conditions: 10'×¼" SE-30 column programmed at 130° C., isothermal). Peaks 201 and 202 are the low boiling by-products of this reaction. Peaks 203, 204 and 205 represent products containing a major proportion of compounds defined according to the structure:

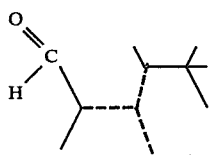

wherein in each of the molecules one of the dashed lines represents a carbon-carbon double bond and each of the other of the dashed lines represent carbon-carbon single bonds.

The peaks indicated by reference numerals 206, 207 and 208 represent starting material, which is a mixture containing a major proportion of isomers defined according to the structure:

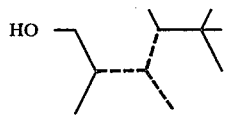

wherein in each of the molecules one of the dashed lines represents a carbon-carbon double bond and each of the other of the dashed lines represent carbon-carbon single bonds.

The resulting product has a fruity, piney aroma with a floral background.

The following Chypre formulation is prepared:

| Ingredients | Parts by Weight |
|---|---|
| Musk ambrette | 40 |
| Musk ketone | 60 |
| Coumarin | 30 |
| Oil of bergamot | 150 |
| Oil of lemon | 100 |
| Methyl ionone | 50 |
| Hexyl cinnamic aldehyde | 100 |
| Hydroxycitronellal | 100 |
| Oil of lavender | 50 |
| Texas cedarwood oil | 85 |
| Virginia cedarwood oil | 30 |
| Oil of sandalwood (East Indies) | 40 |
| Isoeugenol | 20 |
| Eugenol | 10 |
| Benzyl acetate | 30 |
| β-phenyl ethyl alcohol | 40 |
| α-phenyl ethyl alcohol | 30 |
| Oakmoss absolute | 30 |
| Vetiver oil (Venezuela) | 25 |
| $C_{11}$ unsaturated aldehyde mixture of Example II defined according to the structure: 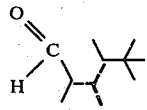 wherein one of the dashed lines in each of the molecules of the mixture is a carbon-carbon double bond and each of the other of the dashed lines represent carbon-carbon single bonds. | 25 |

The $C_{11}$ unsaturated aldehyde composition prepared according to Example II imparts to the Chypre formulation an intense, piney, fruity and floral aroma. The Chypre formulation with the additional intence nuances caused by the use of the product of Example II has advantageous and unexpected properties in the perfume industry.

EXAMPLE IV

PINE FRAGRANCE

The following pine fragrance formulation is produced:

| Ingredients | Parts by Weight |
|---|---|
| Isobornyl acetate | 100 |
| Camphor | 10 |
| Terpeineol | 25 |
| Fir balsam absolute (50% in diethyl phthalate) | 20 |
| Coumarin | 4 |
| Linalool | 30 |
| Fenchyl alcohol | 10 |
| Anethol | 12 |
| Lemon terpenes washed | 50 |
| Borneol | 5 |
| Galbanum oil | 5 |
| Turpentine Russian | 150 |
| Eucalyptol | 50 |
| 2,2,6-trimethyl-1-cyclohexene-1-carboxaldehyde | 12 |
| Laltol (1% in diethyl phthalate) | 5 |
| $C_{11}$ unsaturated aldehyde composition prepared according to Example II containing a mixture of compounds defined according to the structure: 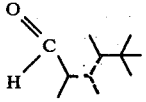 wherein in each of the molecules of the mixture, one of the dashed lines is a carbon-carbon double bond and each of the other of the dashed lines represent carbon-carbon single bond. | 28 |

The $C_{11}$ unsaturated aldehyde prepared according to Example II imparts to this Pine formulation an intense, piney, fruity and floral aroma profile. The Pine formulation with the additional intense nuances caused by the use of the product of Example II has advantageous and unexpected properties in the perfume industry.

EXAMPLE V

PREPARATION OF COSMETIC POWDER COMPOSITIONS

Cosmetic powder compositions are prepared by mixing in a ball mill 100 grams of talcum powder with 0.25 grams of each of the substances set forth in Table I below. Each of the cosmetic powder compositions has an excellent aroma as described in Table I below:

TABLE I

| Substance | Aroma Description |
|---|---|
| Mixture of substances prepared according to Example II and defined according to the structure: [structure shown] wherein in each of the molecules of the mixture, one of the dashed lines represents a carbon-carbon double bond and each of the other of the dashed lines represent carbon-carbon single bonds. | A fruity, piney aroma with a floral background. |
| Perfume composition produced according to Example III. | A chypre type aroma with fruity, piney and floral top notes. |
| Perfume composition prepared according to Example IV. | A piney aroma with fruity and floral undertones. |

EXAMPLE VI

PERFUMED LIQUID DETERGENTS

Concentrated liquid detergents (Lysine salt of n-dodecylbenzene sulfonic acid as more specifically described in U.S. Pat. No. 3,948,818, issued on Apr. 6, 1976 incorporated by reference herein) with aroma nuances as set forth in Table I of Example V, are prepared containing 0.10%, 0.15%, 0.20%, 0.25%, 0.30% and 0.35% of the substance set forth in Table I of Example V. They are prepared by adding and homogeneously mixing the appropriate quantity of substance set forth in Table I of Example V in the liquid detergent. The detergents all posses excellent aromas as set forth in Table I of Example V, the intensity increasing with greater concentrations of substance as set forth in Table I of Example V.

EXAMPLE VII

PREPARATION OF COLOGNES AND HANDKERCHIEF PERFUMES

Compositions as set forth in Table I of Example V are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table I of Example V are imparted to the colognes and to the handkerchief perfumes at all levels indicated.

EXAMPLE VIII

PREPARATION OF SOAP COMPOSITIONS

One hundred grams of soap chips [per sample] (IVORY ®, produced by the Procter & Gamble Company of Cincinnati, Ohio), are each mixed with one gram samples of substances as set forth in Table I of Example V until homogenous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table I of Example V.

EXAMPLE IX

PREPARATION OF SOLID DETERGENT COMPOSITIONS

Detergents are prepared using the following ingredients according to Example I of Canadian Pat. No. 1,007,948 (incorporated by reference herein):

| Ingredient | Percent by Weight |
|---|---|
| "Neodol ® 45-11 (a $C_{14}$–$C_{15}$ alcohol ethoxylanted with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set fourth in Table I of Example V. Each of the detergent samples has an excellent aroma as indicated in Table I of Example V.

EXAMPLE X

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and ther perfuming material are as follows:

1. A water "dissolvable" paper ("Dissolvo Paper")
2. Adogen 448 (m.p. about 140° F.) as the substrate coating; and
3. An outer coating having the following formulation (m.p. about 150° F.):
   57% $C_{20-22}$ HAPS
   22% isopropyl alcohol
   20% antistatic agent
   1% of one of the substances as set forth in Table I of Example V.

Fabric softening compositions prepared according to Example I at column 15 of U.S. Pat. No. 3,632,396 having aroma characteristics as set forth in Table I of Example V, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table I of Example V is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said dryer-added fabric softener non-woven fabrics and these aroma characteristics are described in Table I of Example V, supra.

EXAMPLE XI
HAIR SPRAY FORMULATIONS

The following hair spray formulation is prepared by first dissolving PVP/VA E-735 copolymer manufactured by the GAF Corporation of 140 West 51st Street, New York, N.Y., in 91.62 grams of 95% food grade ethanol. 8.0 grams of the polymer is dissolved in the alcohol. The following ingredients are added to the PVP/VA alcoholic solution:

| | |
|---|---|
| Dioctyl sebacate | 0.05 weight percent |
| Benzyl alcohol | 0.10 weight percent |
| Dow Corning 473 fluid (prepared by the Dow Corning Corporation) | 0.10 weight percent |
| Tween 20 surfactant (prepared by ICI America Corporation) | 0.03 weight percent |
| One of the perfumery substances as set forth in Table I of Example V, supra | 0.10 weight percent |

The perfuming substances as set forth in Table I of Example V add aroma characteristics as set forth in Table I of Example V which are rather intense and aesthetically pleasing to the users of the soft-feel, good-hold pump hair sprays.

EXAMPLE XII
CONDITIONING SHAMPOOS

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepen Chemical Company (35.0 weight percent). The resulting mixture is heated to 60° C. and mixed until a clear solution is obtained (at 60° C.). This material is "COMPOSITION A".

Gafquat ® 755 N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation. This material is "COMPOSITION B".

The resulting COMPOSITION A & COMPOSITION B are then mixed in a 50:50 wt ratio of A:B and cooled to 45° C. and 0.3 wt percent of perfuming substance as set forth in Table I of Example V is added to the mixture. The resulting mixture is cooled to 40° C. and blending is carried out for an additional one hour in each case. At the end of this blending period, the resulting material has a pleasant fragrance as indicated in Table I of Example V.

PATENTS AND PATENT APPLICATIONS INCORPORATED HEREIN BY REFERENCE

The following patents and patent applications referred to, supra, are hereby incorporated herein by reference;

U.S. Ser. No. 160,788 filed on June 19, 1980 U.S. Pat. No. 4,287,084.
U.S. Ser. No. 188,576 filed on Sept. 18, 1980 U.S. Pat. No. 4,303,555.
U.S. Ser. No. 233,861. filed on Feb. 12, 1981 U.S. Pat. No. 4,304,689.
U.S. Ser. No. 267,850 filed on May 28, 1981 U.S. Pat. No. 4,359,412.
U.S. Pat. No. 3,632,396
U.S. Pat. No. 3,948,818
Canadian Pat. No. 1,007,948

What is claimed is:

1. A process for augmenting or enhancing the aroma of a perfume or cologne comprising the step of adding to a perfume or cologne base, an aroma augmenting or enhancing quantity of at least one compound defined according to the generic structure:

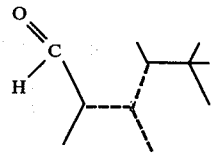

wherein one of the dashed lines represents a carbon-carbon double bond and each of the other of the dashed lines represent carbon-carbon single bonds.

2. A process for augmenting or enhancing the aroma of a perfume or cologne comprising the step of adding to a perfume or cologne base, an aroma augmenting or enhancing quantity of at least one product produced ty the process comprising the steps of (1) intimately admixing one or a mixture of diisoamylene derivatives defined according to the structure:

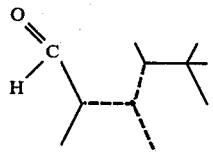

wherein one of the dashed lines represents a carbon-carbon double bond and each of the other of the dashed lines represent a carbon-carbon single bond or produced by the process of reacting a compound having a structure selected from the group consisting of:

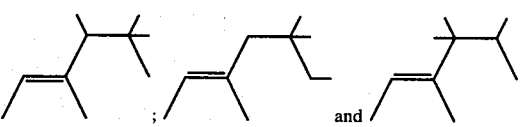

with an alkanoic acid anhydride having the structure:

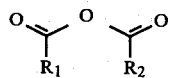

wherein $R_1$ and $R_2$ are the same or different and each represents $C_1$–$C_3$ alkyl; in the presence of an acid catalyst and with formaldehyde or a formaldehyde precursor selected from the group consisting of trioxane, paraformaldehyde and formalin; (2) hydrolyzing in the presence of base the resulting product whereby a mixture containing a major proportion of compounds defined according to the structure:

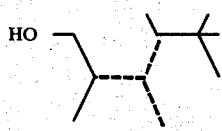

is formed wherein in each of the molecules of the mixture one of the dashed lines represents a carbon-carbon double bond and each of the other of the dashed lines represent carbon-carbon single bonds; and (3) oxidizing the resulting product defined according to the structure:

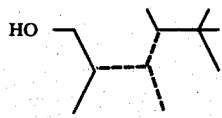

using an oxidizing agent selected from the group consisting of oxygen and air at a temperature and in the range of 200°–500° C. in the presence of a catalyst selected from the group consisting of silver and copper chromite thereby forming a mixture containing a major proportion of isomers defined according to the structure:

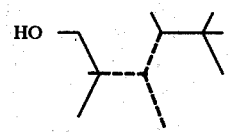

wherein in each of the molecules of the mixture one of the dashed lines represents a carbon-carbon double bond and each of the other of the dashed lines represent carbon-carbon single bonds.

3. A process for augmenting or enhancing the aroma of a perfume or cologne comprising the step of adding to a perfume or cologne base an aroma augmenting or enhancing quantity of at least one product prepared according to the process comprising the step of intimately admixing oxygen or air with a composition of matter comprising a major proportion of compounds defined according to the structure:

wherein in each of the molecules of the mixture one of the dashed lines represents a carbon-carbon double bond and each of the other of the dashed lines represent carbon-carbon single bonds at a temperature in the range of 200°–500° C. in the presence of a catalyst selected from the group consisting of silver and copper chromite.

* * * * *